US010687691B2

(12) United States Patent
Smith et al.

(10) Patent No.: US 10,687,691 B2
(45) Date of Patent: Jun. 23, 2020

(54) ENDOSCOPIC INSTRUMENT HAVING MOVABLE DISTAL TOOL

(71) Applicant: Boston Scientific Scimed, Inc., Maple Grove, MN (US)

(72) Inventors: Paul Smith, Smithfield, RI (US); Barry Weitzner, Acton, MA (US); Naroun Suon, Lawrence, MA (US); Ruth Cheng, Natick, MA (US); Samuel Raybin, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 15/200,271

(22) Filed: Jul. 1, 2016

(65) Prior Publication Data
US 2016/0309988 A1 Oct. 27, 2016

Related U.S. Application Data

(63) Continuation of application No. 13/750,590, filed on Jan. 25, 2013, now Pat. No. 9,408,529.
(Continued)

(51) Int. Cl.
*A61B 1/00* (2006.01)
*A61B 1/018* (2006.01)
(Continued)

(52) U.S. Cl.
CPC ........ *A61B 1/00098* (2013.01); *A61B 1/0052* (2013.01); *A61B 1/0055* (2013.01);
(Continued)

(58) Field of Classification Search
CPC . A61M 1/0058; A61M 1/008; A61B 1/00098; A61B 1/0057; A61B 2017/003;
(Continued)

(56) References Cited

U.S. PATENT DOCUMENTS

| 4,187,849 A | 2/1980 | Stim |
| 4,452,236 A | 6/1984 | Utsugi |

(Continued)

FOREIGN PATENT DOCUMENTS

| EP | 1 426 005 A1 | 6/2004 |
| EP | 1 849 416 A2 | 10/2007 |

(Continued)

OTHER PUBLICATIONS

International Search Report and Written Opinion for corresponding Application No. PCT/US2013/023219 dated Apr. 19, 2013, (12 pages).

*Primary Examiner* — Bhisma Mehta
*Assistant Examiner* — Hamza A Darb
(74) *Attorney, Agent, or Firm* — Bookoff McAndrews, PLLC

(57) ABSTRACT

Embodiments of the disclosure may include a medical device comprising a flexible elongate member including a longitudinal axis and a tool connected to the elongate member near a pivot, wherein the tool may be configured for at least one of suction and infusion, and wherein the tool may be configured to pivot towards both sides of the longitudinal axis relative to the elongate member at the pivot.

20 Claims, 13 Drawing Sheets

Related U.S. Application Data

(60) Provisional application No. 61/590,560, filed on Jan. 25, 2012, provisional application No. 61/592,922, filed on Jan. 31, 2012.

(51) Int. Cl.

| | |
|---|---|
| *A61B 1/015* | (2006.01) |
| *A61B 1/005* | (2006.01) |
| *A61B 1/01* | (2006.01) |
| *A61B 17/32* | (2006.01) |
| *A61M 1/00* | (2006.01) |
| *A61B 17/34* | (2006.01) |
| *A61B 17/00* | (2006.01) |
| *A61B 17/29* | (2006.01) |
| *A61B 17/30* | (2006.01) |

(52) U.S. Cl.
CPC ........ *A61B 1/0057* (2013.01); *A61B 1/00087* (2013.01); *A61B 1/00094* (2013.01); *A61B 1/00119* (2013.01); *A61B 1/01* (2013.01); *A61B 1/015* (2013.01); *A61B 1/018* (2013.01); *A61B 17/320016* (2013.01); *A61B 17/3478* (2013.01); *A61M 1/0058* (2013.01); *A61B 2017/003* (2013.01); *A61B 2017/00314* (2013.01); *A61B 2017/00323* (2013.01); *A61B 2017/2927* (2013.01); *A61B 2017/308* (2013.01); *A61B 2217/005* (2013.01); *A61B 2217/007* (2013.01); *A61M 1/008* (2013.01)

(58) Field of Classification Search
CPC ............ A61B 1/00094; A61B 1/00087; A61B 1/0052; A61B 1/018; A61B 1/0055; A61B 1/00119; A61B 2017/00314; A61B 2017/2927; A61B 2017/00323; A61B 17/3478; A61B 17/320016; A61B 1/015; A61B 1/01; A61B 2017/308; A61B 2217/007; A61B 2217/005
See application file for complete search history.

(56) References Cited

U.S. PATENT DOCUMENTS

| | | | |
|---|---|---|---|
| 5,441,499 A * | 8/1995 | Fritzsch | ........... A61B 17/00234 606/45 |
| 5,704,899 A | 1/1998 | Milo | |
| 6,238,336 B1 | 5/2001 | Ouchi | |
| 6,824,509 B2 | 11/2004 | Yamaya et al. | |
| 7,507,232 B1 | 3/2009 | Garito et al. | |
| 9,226,649 B2 | 1/2016 | Smith et al. | |
| 9,408,529 B2 | 8/2016 | Smith et al. | |
| 9,456,733 B2 | 10/2016 | Smith et al. | |
| 2003/0040657 A1 | 2/2003 | Yamaya et al. | |
| 2003/0073092 A1 | 4/2003 | Hauschild | |
| 2003/0073902 A1 | 4/2003 | Hauschild et al. | |
| 2004/0186368 A1 | 9/2004 | Ramzipoor | |
| 2006/0289602 A1 | 12/2006 | Wales et al. | |
| 2007/0270895 A1 * | 11/2007 | Nobis | ................ A61B 17/3478 606/170 |
| 2007/0276430 A1 * | 11/2007 | Lee | .................... A61B 1/00071 606/205 |
| 2007/0282353 A1 | 12/2007 | Surti | |
| 2008/0167665 A1 | 7/2008 | Arp et al. | |
| 2009/0012517 A1 | 1/2009 | de la Rama et al. | |
| 2009/0171349 A1 | 7/2009 | Byrd et al. | |
| 2009/0275967 A1 * | 11/2009 | Stokes | ................ A61B 17/1114 606/172 |
| 2010/0076266 A1 | 3/2010 | Boulais et al. | |
| 2010/0168718 A1 | 7/2010 | Bellisario et al. | |
| 2010/0222677 A1 | 9/2010 | Placek et al. | |
| 2010/0280316 A1 | 11/2010 | Dietz et al. | |
| 2011/0224647 A1 | 9/2011 | Lazarus | |
| 2016/0081532 A1 | 3/2016 | Smith et al. | |

FOREIGN PATENT DOCUMENTS

| | | |
|---|---|---|
| EP | 1 857 061 | 11/2007 |
| JP | 55-012953 | 7/1978 |
| JP | 63-292935 A | 11/1988 |
| JP | 7-163574 | 6/1995 |
| JP | H09-503677 A | 4/1997 |
| JP | 2000-254146 A | 9/2000 |
| JP | 2000-512526 A | 9/2000 |
| JP | 2004-194740 A | 7/2004 |
| JP | 2005-103268 A | 4/2005 |
| JP | 2007-307371 A | 11/2007 |
| JP | 2007-535972 A | 12/2007 |
| JP | 2010-042115 A | 2/2010 |
| JP | 2010-526598 A | 8/2010 |
| JP | 2011-015838 A | 1/2011 |
| JP | 2011-183165 A | 9/2011 |
| WO | WO 99/05975 A1 | 2/1999 |
| WO | WO 02/094353 | 11/2002 |
| WO | WO 2006/048966 A1 | 5/2006 |
| WO | WO 2010/100780 A1 | 9/2010 |

* cited by examiner

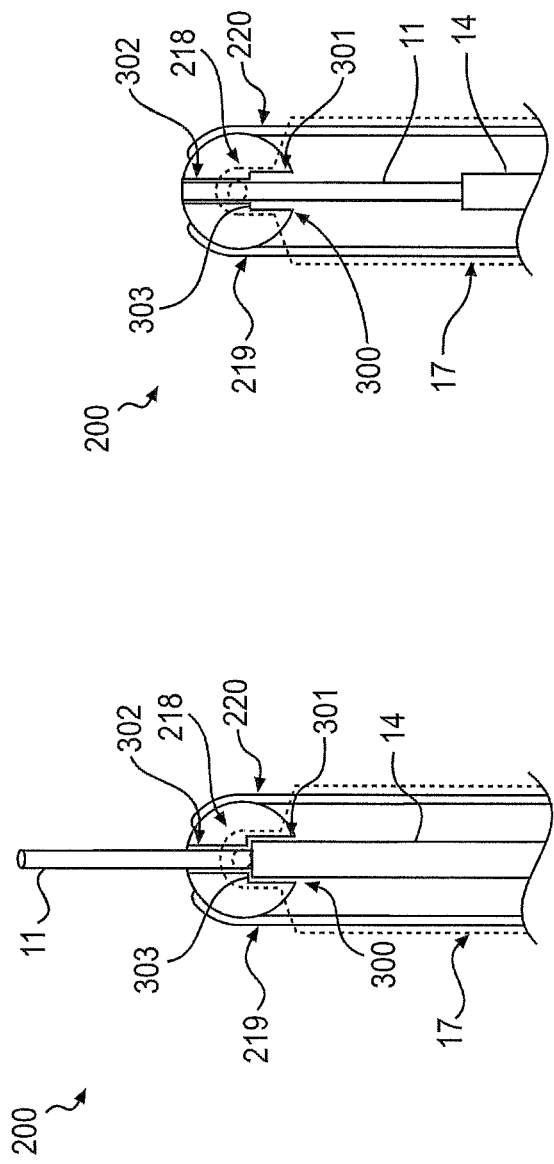

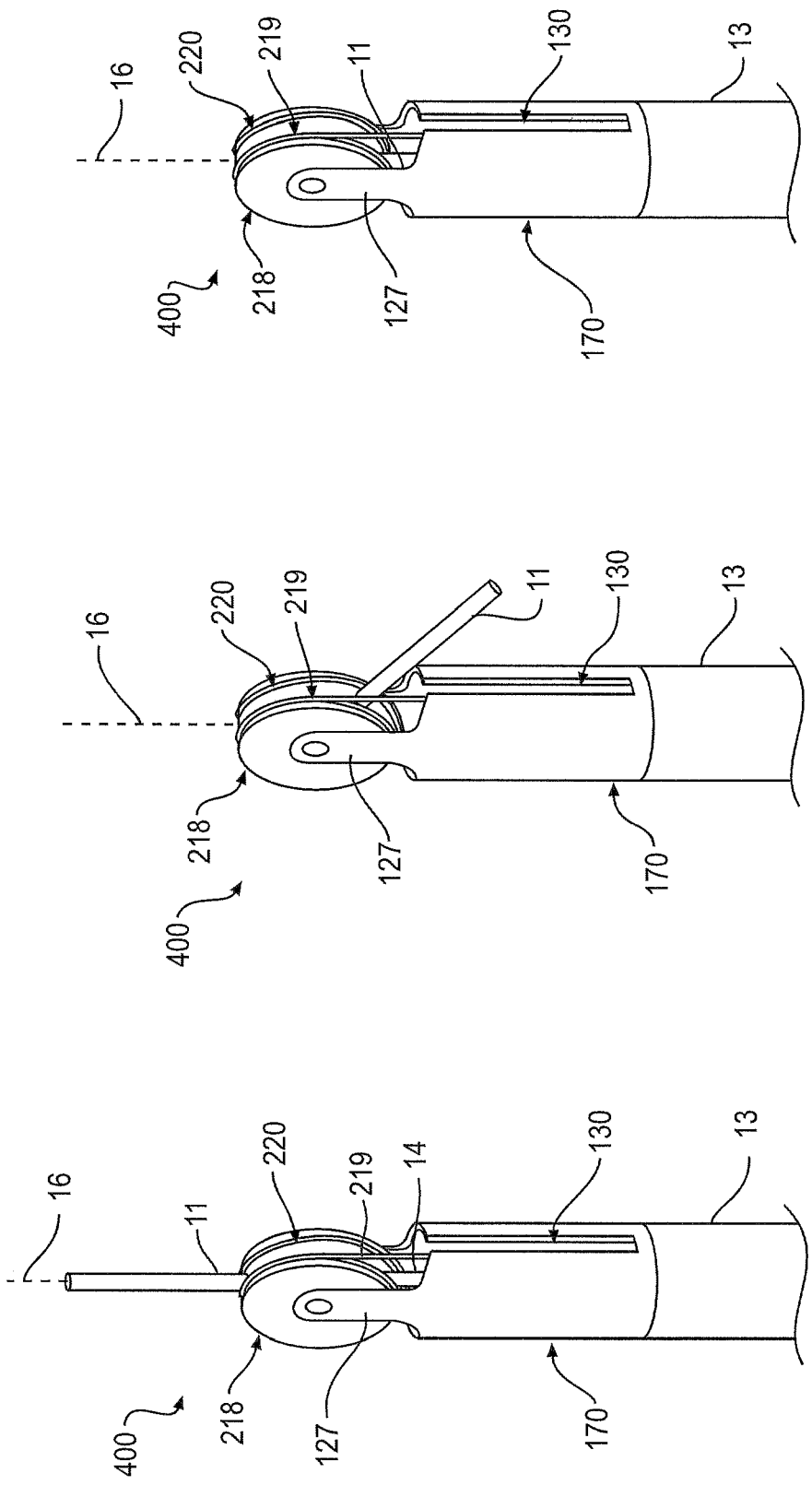

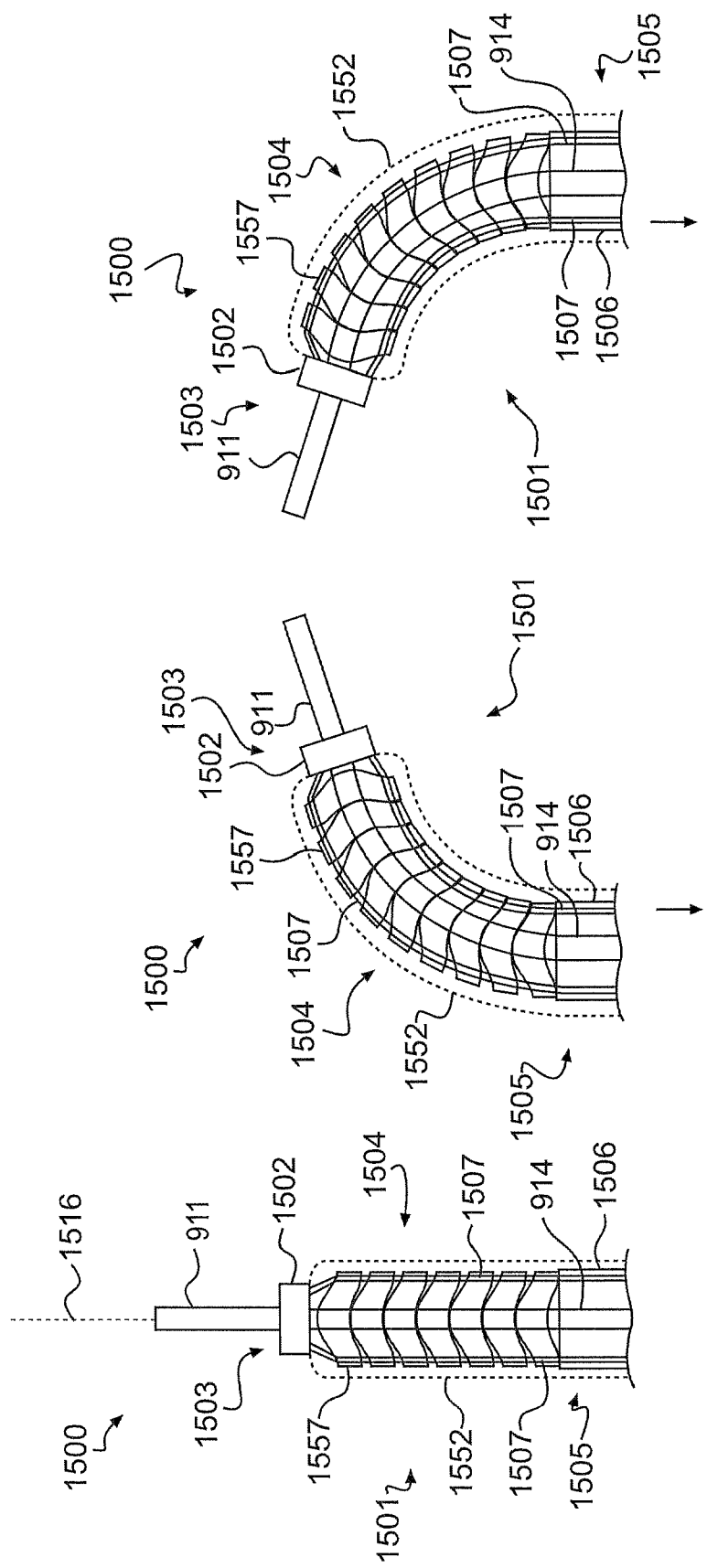

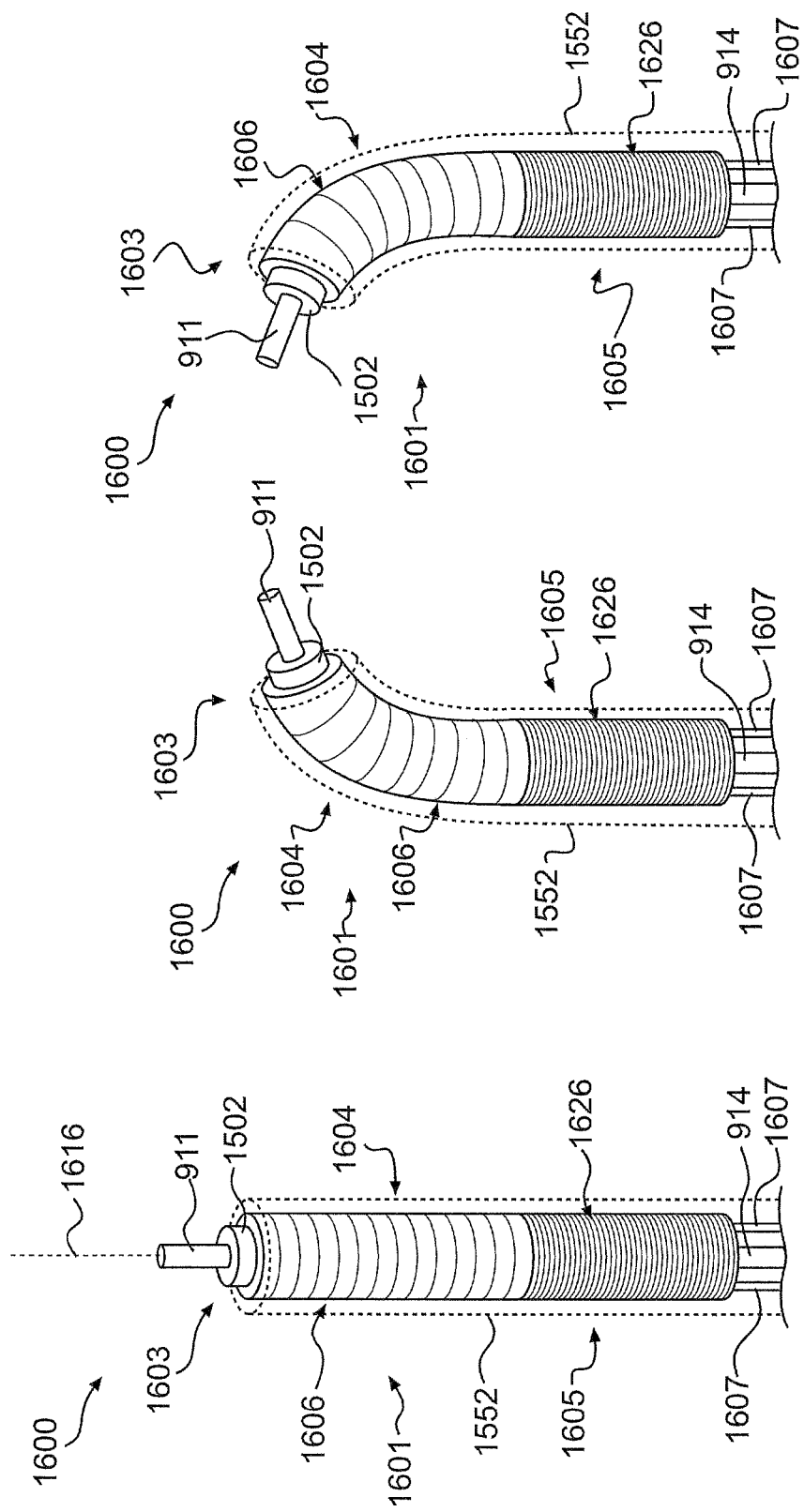

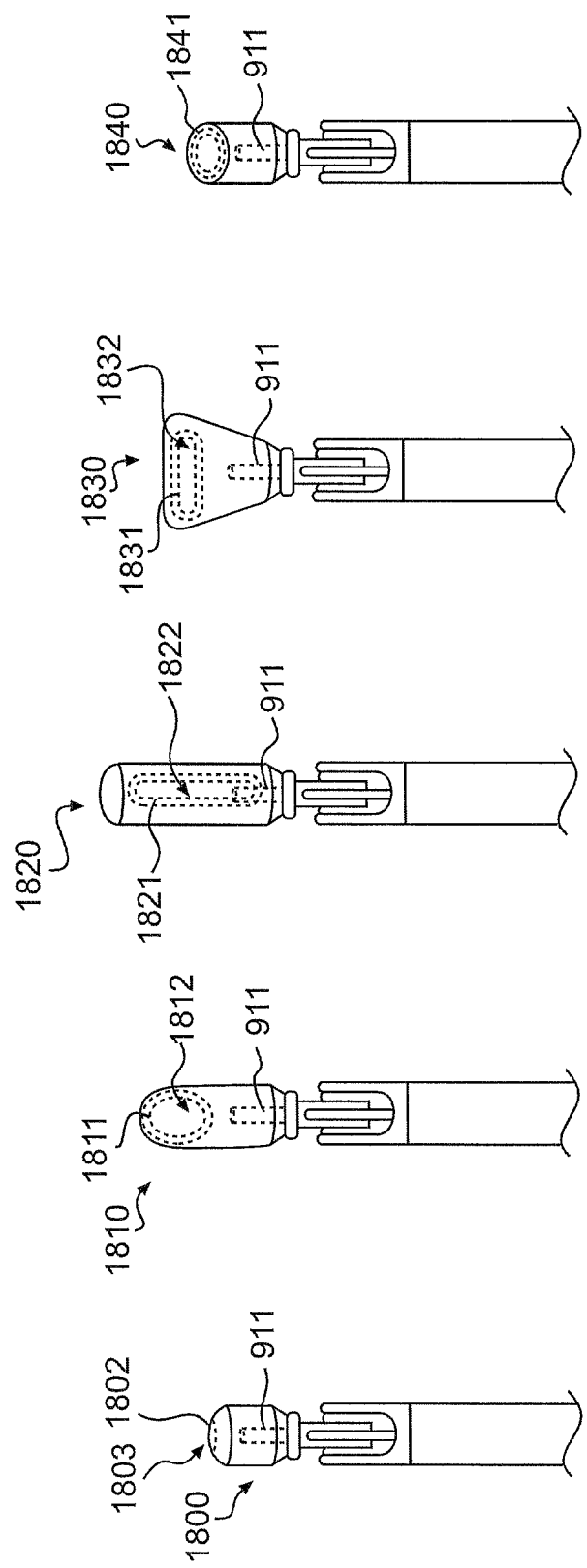

ENDOSCOPIC INSTRUMENT HAVING MOVABLE DISTAL TOOL

This application is a Continuation of U.S. application Ser. No. 13/750,590, filed Jan. 25, 2013, now U.S. Pat. No. 9,408,529, issued on Aug. 9, 2016, which claims the benefit of U.S. Provisional Application No. 61/590,560, filed Jan. 25, 2012, and U.S. Provisional Application No. 61/592,922, filed Jan. 31, 2012, the disclosures of which are incorporated herein in their entirety.

FIELD OF THE DISCLOSURE

Embodiments of the present disclosure include medical devices, and more particularly, endoscopic instruments having a movable distal tool including, for example, a deflectable and retractable injection needle, and a deflectable suction device, and related methods of using such medical devices.

BACKGROUND OF THE DISCLOSURE

Generally speaking, endoscopes may be used for various diagnostic and medical procedures. Endoscopes may be used in the diagnosis and treatment of a wide range of diseases and disorders that typically require a physician to access and navigate internal anatomical lumens within a patient's body and body cavities, such as the abdomen. Once the endoscope is positioned in a desired body portion, a treatment instrument may be advanced through a working channel of the endoscope to the desired body portion.

For example, in certain tissue dissection procedures, a resection device, such as a needle or a surgical blade, may be directed through the working channel of the endoscope, and the endoscope may be maneuvered to a desired tissue location. The resection device may include one or more sharp edges or points configured to cut certain target tissue for treatment or examination purposes.

Due to the sharp edges and points on the resection device, the potential for undesired damage to the walls of the working channel and, in some cases, non-targeted tissue, exists. The medical device and related methods of the present disclosure are directed to improvements in the existing technology.

As another example, in certain tissue dissection procedures, a suction device, such as a suction tube, may be directed through the working channel of the endoscope, and the endoscope may be maneuvered to a desired tissue location. The suction device may be configured to grasp certain target tissue for manipulation by other endoscopic instruments, for example, forceps, graspers, snares, probes, scissors, knives, retrieval devices, lasers, and, the like.

A conventional suction device may be positioned relative to the target tissue by movement of the endoscope. In other words, the endoscope is articulated, steered, shifted, pulled, and/or pushed by the physician to place the suction device at or near the target tissue. A second operator, such as another physician or a physician's assistant, may then control the operation of the suction device once positioned at or near the target tissue.

Adjusting the position of the suction device by moving the endoscope may be time consuming, cumbersome, and not accurate. In addition, moving the endoscope to move the suction device may also undesirably move other instruments. Accordingly, a need exists to simplify the manner and improve the accuracy in which the position of suction device is adjusted. The suction device and related methods of the present disclosure are directed to improvements in the existing technology.

SUMMARY OF THE DISCLOSURE

In accordance with an embodiment, a medical device may include a flexible elongate member including a longitudinal axis and a tool connected to the elongate member at a pivot, wherein the tool may be configured to pivot towards at least one side of the longitudinal axis relative to the elongate member at the pivot, and wherein the tool may be configured to move between an extended position and a retracted position along the longitudinal axis.

Various embodiments of the disclosure may include one or more of the following aspects: a clevis and a pivoting member held by the clevis and rotatable relative to the clevis; the pivoting member may include a lumen, and wherein the tool may extend through the lumen; the tool may be movable to the extended position by distally advancing the tool through the lumen, and the tool may be movable to the retracted position by proximally retracting the tool through the lumen; the lumen may include a stop configured to prevent the tool from distal advancement beyond a predetermined position; a delivery tube fluidly coupled to the tool, wherein the delivery tube may be configured to abut against the stop to prevent the tool from distal advancement beyond the predetermined position; the delivery tube and the tool are integrally formed; a sleeve configured to cover the tool, and wherein the tool may be configured to move between the extended position and the retracted position by relative axial movement between the tool and the sleeve; at least one actuation member configured to actuate axial movement of the sleeve; a first control member and a second control member connected to the pivoting member at different points of the pivoting member, and wherein actuation of the first and second control members may cause the tool to pivot towards either side of the longitudinal axis; the tool may include a blade; the tool may be configured for axial movement relative to the lumen to cause an axial cutting motion of the blade; the blade may include serrated teeth; the tool may include a double-edged blade; the blade may be electrically conductive; the tool may include a curved blade; and the tool may include a curved blade including a concave section have a sharp edge and a convex section having a dull edge.

In accordance with another embodiment, a medical device may include a flexible elongate member including a longitudinal axis and a tool connected to the elongate member at a pivot, wherein the tool may be configured to pivot towards at least one side of the longitudinal axis relative to the elongate member at the pivot, and wherein the tool may be configured to move between an extended position and a retracted position by pivoting about the pivot.

Various embodiments of the disclosure may include one or more of the following aspects: a clevis including a slot, and a pivoting member held by the clevis and rotatable relative to the clevis, wherein the tool may be operably coupled to the pivoting member, and wherein, in the retracted position, the pivoting member may rotate and the tool may enter the slot; a first control member wrapped around the circumference of the pivoting member on a first position of the pivoting member, wherein the tool may be deflected in a first direction when the first control member is proximally retracted; and a second control member wrapped around the circumference of the pivoting member on a second position of the pivoting member, wherein the tool may be deflected in a second direction different than the first direction when the second control member is proximally retracted.

In accordance with yet another embodiment, a medical device may include a flexible elongate member, a tool, and a pivoting member that rotates relative to the elongate member. The pivoting member may include a lumen extending through the pivoting member, wherein the tool may be operably coupled to the pivoting member and configured to pivot towards either side of the elongate member by actuation of the pivoting member, and wherein the tool may be configured to move to an extended position by distally advancing the tool through the lumen and move to a retracted position by proximally retracting the tool through the lumen.

Various embodiments of the disclosure may include the following aspect: the lumen may include a stop configured to prevent the tool from distal advancement beyond a predetermined position.

In accordance with an embodiment, a medical device may include a flexible elongate member including a longitudinal axis and a tool connected to the elongate member near a pivot, wherein the tool may be configured for one of suction and infusion, and wherein the tool may be configured to pivot towards both sides of the longitudinal axis relative to the elongate member at the pivot.

Various embodiments of the disclosure may include one or more of the following aspects: a positioning mechanism, wherein actuation of the positioning mechanism may cause the tool to pivot; the positioning mechanism may include a clevis, a pivoting member held by the clevis and rotatable relative to the clevis, and a first control member and a second control member operably coupled to the pivoting member, wherein the tool may be operably coupled to the pivoting member; the tool may be deflected in a first direction when the first control member is proximally retracted, and the tool may be deflected in a second direction opposite the first direction when the second control member is proximally retracted; a suction tube may be configured to fluidly couple the tool to a vacuum source; the suction tube may include a flexible distal portion comprising of an inner braid reinforced by a polymeric sheath; the tool may be a hollow tube with a distal opening, wherein suction through the tool may cause the hollow tube to grasp tissue; the distal opening may be configured to form a fluidic seal between the hollow tube and tissue; an outer hollow container surrounding the hollow tube, the container defining an opening; the opening may be a side-facing opening; the opening may be a distal-facing opening; a handle assembly coupled to the flexible elongate member, wherein the handle assembly may include a deflection actuator configured to actuate the first and second control members, and a suction actuator configured to control suction of the tool; the suction actuator may be configured to selectively allow and block aspiration through the suction tube; and a distal portion of the elongate member may include a plurality of pivoting links configured to deflect the distal portion.

In accordance with another embodiment, a medical device may include a flexible elongate member including a longitudinal axis, a tool configured for suction, and a pivoting member, wherein the tool may be operably coupled to the pivoting member and configured to pivot towards at least one side of the longitudinal axis relative to the elongate member by actuation of the pivoting member, wherein the pivoting member may include a lumen extending to the tool.

Various embodiments of the disclosure may include one or more of the following aspects: a suction tube configured to fluidly couple the tool to a vacuum source; and a first control member and a second control member operably coupled to the pivoting member, wherein the tool may be deflected in a first direction when the first control member is proximally retracted, and the tool may be deflected in a second direction opposite the first direction when the second control member is proximally retracted.

In accordance with yet another embodiment, a medical device may include a flexible elongate member, a tool configured for suction, a pivoting member, wherein the tool may be operably coupled to the pivoting member, a first control member operably coupled to the pivoting member at a first side of the pivoting member, and a second control member operably coupled to the pivoting member at a second side of the pivoting member opposite the first side, wherein the tool may be configured to pivot towards both sides of the elongate member by actuation of the first and second control members.

Various embodiments of the disclosure may include one or more of the following aspects: the tool may be deflected in a first direction when the first control member is proximally retracted, and the tool may be deflected in a second direction opposite the first direction when the second control member is proximally retracted; and a suction tube configured to fluidly couple the tool to a vacuum source, wherein the suction tube may include a flexible distal portion formed of an inner braid reinforced by a polymeric sheath.

In this respect, before explaining multiple embodiments of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

FIG. 3A illustrates a cross-sectional view of the injection needle of FIGS. 2A-2C in an extended configuration, according to an exemplary disclosed embodiment;

FIG. 3B illustrates a cross-sectional view of the injection needle of FIGS. 2A-2C in a retracted configuration, according to an exemplary disclosed embodiment;

FIG. 4A illustrates a schematic view of another injection needle, according to an exemplary disclosed embodiment;

FIG. 4B illustrates a schematic view of the injection needle of FIG. 4A in a partially-retracted configuration, according to an exemplary disclosed embodiment;

FIG. 4C illustrates a schematic view of the injection needle of FIG. 4A in a fully-retracted configuration, according to an exemplary disclosed embodiment;

FIG. 10A illustrates a schematic view of another suction device, according to an exemplary disclosed embodiment;

FIG. 10B illustrates another schematic view of the suction device of FIG. 10A, according to an exemplary disclosed embodiment;

FIG. 10C illustrates another schematic view of the suction device of FIG. 10A, according to an exemplary disclosed embodiment;

FIG. 11A illustrates a schematic view of another suction device, according to an exemplary disclosed embodiment;

FIG. 11B illustrates another schematic view of the suction device of FIG. 11A, according to an exemplary disclosed embodiment;

FIG. 11C illustrates another schematic view of the suction device of FIG. 11A, according to an exemplary disclosed embodiment;

FIG. 13A illustrates a cup device for a suction device, according to an exemplary disclosed embodiment;

FIG. 13B illustrates another cup device for a suction device, according to an exemplary disclosed embodiment;

FIG. 13C illustrates another cup device for a suction device, according to an exemplary disclosed embodiment;

FIG. 13D illustrates another cup device for a suction device, according to an exemplary disclosed embodiment; and FIG. 13E illustrates another cup device for a suction device, according to an exemplary disclosed embodiment.

DETAILED DESCRIPTION

Reference will now be made in detail to the exemplary embodiments of the present disclosure described above and illustrated in the accompanying drawings.

The terms "proximal" and "distal" are used herein to refer to the relative positions of the components of an exemplary endoscopic instrument. When used herein, "proximal" refers to a position relatively closer to the exterior of the body or closer to the physician, or other user, using the endoscopic instrument. In contrast, "distal" refers to a position relatively further away from the surgeon, or other user, using the endoscopic instrument or closer to the interior of the body.

Figure 1:
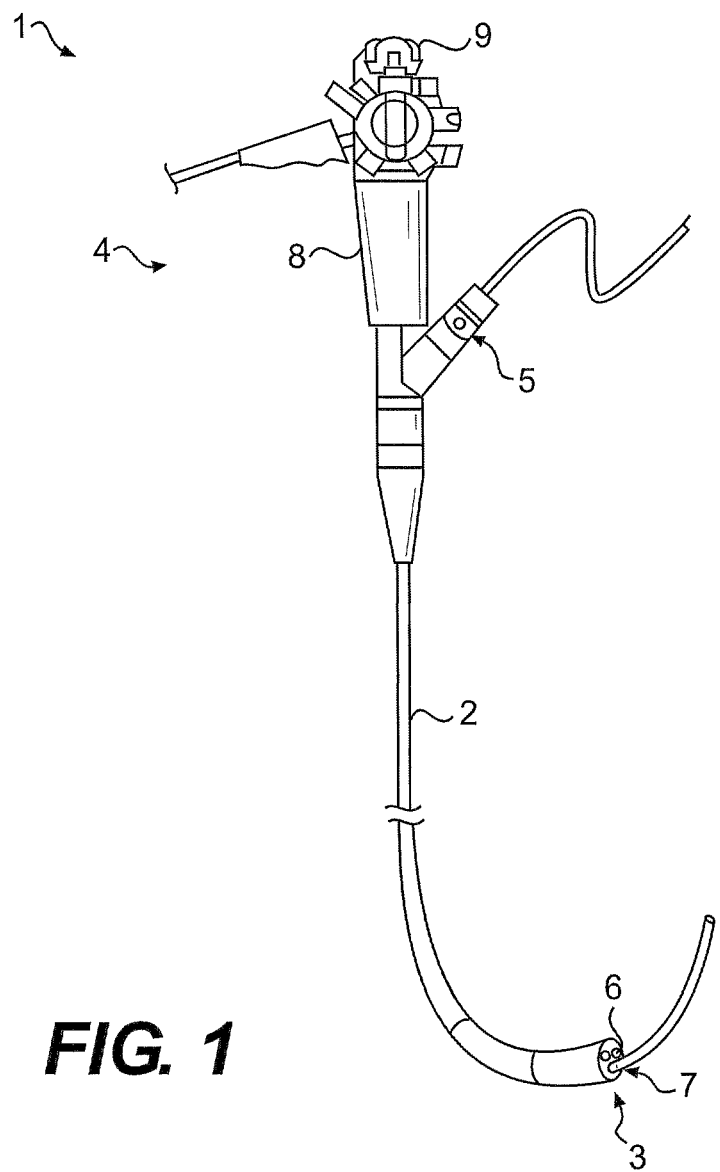
FIG. 1 illustrates an endoscope for use with one or more devices, according to an exemplary disclosed embodiment.

FIG. 1 illustrates an endoscope 1 according to an exemplary embodiment. Endoscope 1 may include a flexible outer tube 2 extending between a distal end 3 and a proximal end 4 of endoscope 1. Endoscope 1 may further include at least one treatment instrument port 5 for receiving a treatment device, such as a suction device, an injection needle, electrocautery needle, forceps, and any other suitable device known in the art, into at least one working channel 6 of endoscope 1. The at least one working channel 6 may extend within endoscope 1 and terminate at distal end 3 at an opening 7. Although opening 7 is illustrated as being defined on a distal face of outer tube 2, it should also be appreciated that one or more openings 7 may be defined on a side surface of outer tube 2.

Endoscope 1 may also include a handle 8 at proximal end 4. Handle 8 may include various positioning controls 9 to effectuate bending and rotation of flexible outer tube 2 for positioning endoscope 1 and any treatment instruments during a medical procedure.

The present disclosure may relate to endoscopic instruments that may include various types of end effectors, or tools, at the distal end of the endoscopic instrument that may require precise positioning within an anatomical lumen. The present disclosure describes embodiments of injection needles, suction devices, and irrigation devices. Other types of tools, however, may be substituted for those devices, including, as examples and not limited to, biopsy forceps, graspers, scissors, knives, needle knives, probes, dissectors, scrapers, cautery electrodes, and suction probes.

Figure 2A:
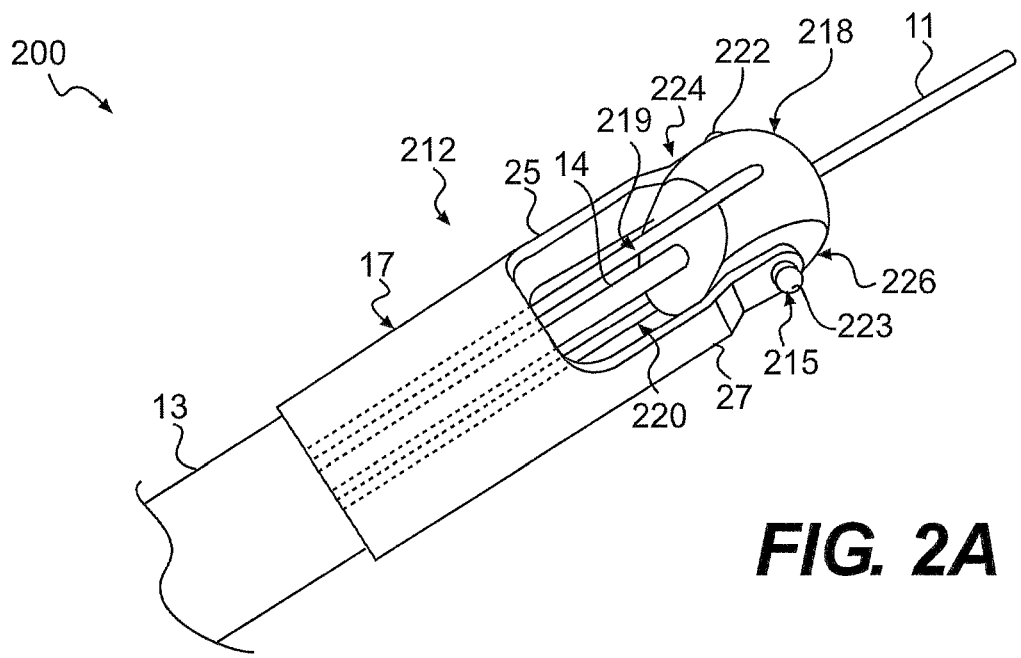
FIG. 2A illustrates a schematic view of an injection needle, according to an exemplary disclosed embodiment.
Figure 2B:
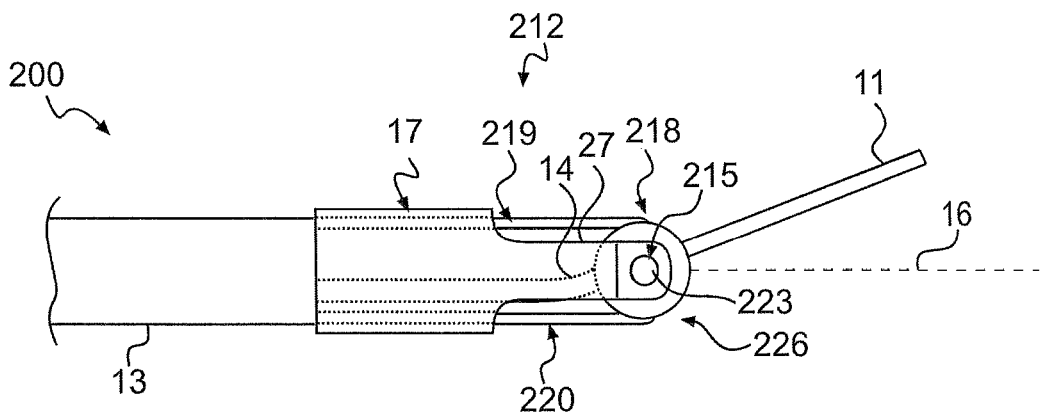
FIG. 2B illustrates another schematic view of the injection needle of FIG. 2A, according to an exemplary disclosed embodiment.
Figure 2C:
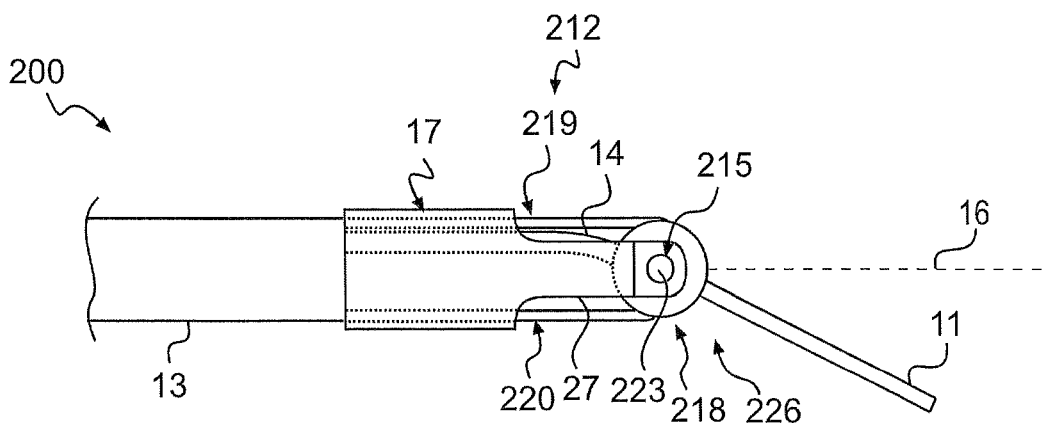
FIG. 2C illustrates another schematic view of the injection needle of FIG. 2A, according to an exemplary disclosed embodiment.

FIGS. 2A-2C illustrate an injection needle 200 according to an exemplary disclosed embodiment. Injection needle 200 may extend through the at least one working channel 6 of endoscope 1 and exit opening 7 to reach a desired treatment location. Injection needle 200 may be configured to, for example, irrigate fluids at a treatment site, inject vasoconstrictor fluid into a vessel to slow hemorrhaging, inject a sclerosing agent to control bleeding varices by hardening targeted tissues, inject suitable fluids for creating a bleb at the treatment location, inject fluids into tissue at the treatment location to separate tissue planes, inject fluidic dyes, such as Indigo Carmine, for visualization purposes, inject drugs, and inject bulking agents. In certain other embodiments, injection needle 200 may be configured to aspirate fluids and/or tissue.

As illustrated in FIG. 2A, injection needle 200 may include a distal tool 11, a positioning mechanism 212, and a flexible tube 13. Distal tool 11 may be hollow and include a lumen fluidly coupled to a delivery tube 14 extending through flexible tube 13. In some embodiments, distal tool 11 may be a hypotube. A flexible stylet may be positioned in the lumen of distal tool 11 to provide structural strength for distal tool 11 and block the entry of tissue. A suitable fluid may be delivered from a fluid source (not shown), through delivery tube 14, and out of a distal opening of distal tool 11. Distal tool 11 may comprise any material capable of conducting electricity, such as, for example, stainless steel, nickel titanium alloys, and the like. All or one or more portions of distal tool 11 may comprise the conducting material. A distal end of distal tool 11 may be relatively sharp for piercing tissue. Alternatively, the distal end of distal tool 11 may be relatively blunt and may penetrate tissue via an electrical current running through distal tool 11, as will be described in more detail below. By being relatively blunt, injection needle 10 may be advanced through the at least one working channel 6 of endoscope 1 without skiving the walls of channel 6. A proximal end of distal tool 11 may be operably coupled to positioning mechanism 212.

Positioning mechanism 212 may be configured to rotate, or deflect, distal tool 11 of injection needle 200 around a pivot 215. In other words, and as shown in FIGS. 2B-2C, distal tool 11 may pivot in a lateral direction relative to a longitudinal axis 16 of flexible tube 13 by actuation of positioning mechanism 212. Positioning mechanism 12 may include a clevis member 17, a pivoting member 218, a first control member 219, and a second control member 220. First and second control members 219 and 220 may include any suitable coupling device, such as, for example, a wire, a rod, or a hollow tube.

Clevis member 17 may be disposed on a distal end of flexible tube 13. A proximal portion of clevis member 17 may be positioned over flexible tube 13 and may be hollow to provide communication between flexible tube 13 and pivoting member 218. Alternatively, the proximal portion of clevis member 17 may be under (or within) flexible tube 13, or abut against flexible tube 13.

Pivoting member 218 may be positioned within clevis member 17 and coupled to clevis member 17 via a first pin (or boss) 222 and a second pin (or boss) 223. First pin 222 may extend from a first side 224 of pivoting member 218 and may rotatably connect pivoting member 218 to first arm 25 of clevis member 17. Second pin 223 may extend from a second side 226 of pivoting member 218 and may rotatably connect pivoting member 218 to second arm 27 of clevis member 17. Accordingly, pivoting member 218 may be configured to rotate about first pin 222 and second pin 223.

A distal portion of first control member 219 may be anchored to pivoting member 218 on a first point of pivoting member 218, and a distal portion of second control member 220 may be anchored to pivoting member 218 on a second point different than the first point of pivoting member 218. For example, first control member 219 and second control member 220 may be positioned on opposite sides of pivoting member 218. First and second control members 219, 220 may be anchored to pivoting member 218 by any suitable means, such as, for example, adhesives, welding, crimping, fasteners, anchors, and the like. Moreover, first and second control members 219, 220 may be substantially aligned with each other and may be positioned on opposite sides of distal tool 11. As will be discussed in more detail below, delivery tube 14 and distal tool 11 may extend through pivoting member 218 between first and second members 219, 220.

An appropriate handle assembly (not shown) may be operably coupled to first control member 219 and second control member 220 external endoscope 1 and may manipulate first and second control members 219, 220. Any suitable, known handle assembly may be used, including spool-type handles or scissor-like handles. As shown in FIG. 2B, the handle assembly may be actuated to retract first control member 219 in a proximal direction. That is, first control member 219 may be pulled back, causing pivoting member 218 to rotate, and thus the deflection of distal tool 11 in a first direction. As shown in FIG. 2C, the handle assembly may be actuated to retract second control member 220 in a proximal direction (i.e., pulled back), causing pivoting member 218 to rotate, and thus the deflection of distal tool 11 in a second direction opposite the first direction. Therefore, an angle between distal tool 11 and longitudinal axis 16 may be altered upon actuation of first and second control members 219, 220. It should be appreciated, however, that injection needle 200 may include any suitable restriction means to regulate the range of motion of distal tool 11. For example, the handle assembly may include appropriate stops configured to limit the length of first control member 219 and/or second control member 220 that may be retracted. Alternatively, mechanism 212 could include appropriate stops to limit the range of motion of tool 11. Moreover, in certain embodiments, the handle assembly may include an appropriate locking mechanism to lock distal tool 11 in any suitable position. For example, the locking mechanism may secure distal tool 11 in a deflected position, and may release the distal tool 11 from the deflected position when desired.

In other embodiments, one or both of first control member 219 and second control member 220 may be designed to be distally advanced to cause pivoting member 218 to rotate. Furthermore, it should be appreciated that pivoting member 218 may be designed to pivot eccentrically, and may include any suitable shape such as, for example, a circular disk, a spherical shape, a cylindrical shape, or any other symmetrical or asymmetrical profile (e.g., a cam-shaped surface).

As discussed above, distal tool 11 may be electrically conductive to act as a electrosurgical treatment instrument. For example, distal tool 11 may coagulate, cauterize, dissect, burn, and/or cut target tissue upon being energized by an electrical current. Moreover, distal tool 11 may be configured to perform monopolar or bipolar cauterization. Such electrosurgical treatment by distal tool 11 may be performed as distal tool 11 is deflected about pivot 215. In addition, the electrosurgical treatment by distal tool 11 may be performed in conjunction with the fluid delivery feature of injection needle 10. For example, fluid may be injected though distal tool 11 at a tissue treatment site to separate certain tissue layers, such as an adenoma from its underlying tissue. Distal tool 11 may then become electrically activated and cauterize and resect the adenoma.

In one exemplary embodiment, one or both of first control member 219 and second control member 220 may provide an electrical pathway from a source of electrical current (not shown) to distal tool 11. The handle assembly may include an appropriate connector for connection to, for example, a source of radio frequency (RF) energy. The energy may be conducted through the handle assembly to one or both of first control member 219 and second control member 220. One or both of first control member 219 and second control member 220 and pivoting member 218 may comprise any material capable of conducting electricity, such as, for example, stainless steel, nickel titanium alloys, and the like. Contact between distal tool 11 and pivoting member 218 may provide an electrical connection for electricity delivered through one or both of first control member 219 and second control member 220. Additionally, or alternatively, one or more separate conductive wires, cables, sheaths, or the like may be twisted along, adjacent to, formed within, or physically separated from one or both of first control member 219 and second control member 220 and may provide the electrical pathway to distal tool 11. Clevis member 17 may also be formed of any material capable of conducting electricity; however, the surface of clevis member 17 may be covered with a suitable insulating material, such as, for example a powder coat or non-conducting polymeric sheath, to minimize the discharge and effects of any stray electrical energy from clevis member 17. Insulation of clevis member 17 may also prevent electrical energy from causing tissue damage due to incidental contact with clevis member 17. Similarly, flexible tube 13 may be formed of any non-conducting polymer material, or may be coated with an insulating polymer material incapable of conducting electricity.

It should also be appreciated that one or both of first control member 219 and second control member 220 and pivoting member 218 may be covered with a suitable insulating material. For example, an insulating sheath may cover one or both of first control member 219 and second control member 220, and the surface of pivoting member 218 may be powder coated with an insulating material. Suitable insulation material may also be utilized anywhere on injection needle 200 to prevent any undesired electrical pathways. The insulating material may include a polymer, a ceramic, or any other suitable non-conductive material.

Additionally, or alternatively, delivery tube 14 may provide an electrical pathway from the source of electrical current to distal tool 11. In such an arrangement, delivery tube 14 may include a coil or a wire formed of any suitable material capable of conducting electricity in direct contact with distal tool 11. A sheath formed of an insulating polymer material may cover the coil to prevent the discharge and effects of stray electrical energy from delivery tube 14. In another embodiment, delivery tube 14 may be a sheath formed of an insulating polymer material. A conductive member may be attached to an interior wall of the sheath and may be directly connected to distal tool 11, thereby providing an electrical path from the source of electrical current to distal tool 11. Alternatively, the conductive member may be attached to an outside surface of the sheath and may be electrically connected to pivoting member 218. Electrical energy may therefore travel from pivoting member 218 to distal tool 11. It should be appreciated that the conductive member may also be covered with a suitable insulating material to prevent the discharge and effects of any stray electrical energy.

Accordingly, injection needle 200 may provide the ability for distal tool 11 to be adjusted independently of endoscope 1, that is, the position of distal tool 11 may be altered by manipulating positioning mechanism 212, without the need to articulate, steer, shift, pull, and/or push endoscope 1. Finer control of the position of distal tool 11 may therefore be provided to a physician. In addition, the physician may be able to maneuver and control injection needle 200, without assistance from a second operator, such as another physician or a physician's assistant. The physician may directly and simultaneously control the position and activation (i.e., fluid delivery and electrocauterization) of injection needle 200. Moreover, when using injection needle 200 with an endoscope housing multiple tools, the position of injection needle 200 may be independently controlled without moving the other tools, since the entire endoscope need not be manipulated to position injection needle 200.

FIG. 3A illustrates a cross-sectional view of injection needle 200 in an extended configuration according to an exemplary embodiment. As shown in FIG. 3A, pivoting member 218 may include an open lumen 300 extending from a proximal end to a distal end of pivoting member 218. At least a portion of distal tool 11 and delivery tube 14 may extend through lumen 300. As alluded to above, delivery tube 14 may be fluidly coupled to tool 11. Accordingly, delivery tube 14 may be connected to tool 11 by any suitable means, such as, for example, adhesives, welding, friction fit, crimping, swaging, and the like. Alternatively, delivery tube 14 and tool 11 may be integrally formed, in which tool 11 may be a rigid extension of delivery tube 14, such as, for example, a tapered portion at the distal end of delivery tube 14. Delivery tube 14 may be formed of any suitable flexible material to accommodate bending and deflection of delivery tube 14 upon rotation of pivoting member 218 but rigid enough to effectuate axial translation of distal tool 11 and delivery tube 14 through lumen 300. In certain embodiments, for example, delivery tube 14 may comprise a flexible portion structurally designed for increased flexibility, such as a bellows. Delivery tube 14 may be composed of one or more of metals, plastics, polymers, and elastomers, and may be formed of multiple materials to vary the flexibility and the stiffness along delivery tube 14. In certain embodiments, a distal portion of delivery tube 14 may be more flexible then a proximal portion of delivery tube 14 to accommodate bending. For example, the distal portion of delivery tube 14 may be formed of a metallic spring or coil covered by a flexible material, such as a polymeric sheath, and the proximal portion of delivery tube 14 may be formed of a stiff, polymeric tube.

Distal tool 11 may be placed in an extended position, as shown in FIG. 3A. That is, distal tool 11 may be distally advanced and extend outside of lumen 300 at the distal end of pivoting member 218. In the extended position, at least a portion of delivery tube 14 and tool 11 may extend through lumen 300. More specifically, lumen 300 may include a first portion 301 having a first diameter and a second portion 302 having a second diameter smaller than the first diameter of first portion 301. The first diameter of first portion 301 may be sized to allow axial movement of distal tool 11 and delivery tube 14 therethrough. The widths of both the distal tool 11 and delivery tube 14 may be smaller than the first diameter such that distal tool 11 and delivery tube 14 may freely move within first portion 301. The second diameter of second portion 302 may be sized to allow axial movement of distal tool 11 therethrough but may not allow access of delivery tube 14. In other words, the meeting point of first portion 301 and second portion 302 forms a stop 303 defined by the walls of lumen 300 such that delivery tube 14 (and thus distal tool 11) may be prevented from distal advancement beyond a predetermined position. The width of distal tool 11 may be smaller than the second diameter of second portion 302 such that distal tool 11 may freely move within second portion 302, and the width of delivery tube 14 may be larger than the second diameter of second portion 302 such that delivery tube 14 may abut against stop 303 and be restricted from entering second portion 302. Alternatively, in certain embodiments, distal tool 11 and delivery tube 14 may have substantially the same diameters. A suitable shoulder structure (not shown) may be positioned between distal tool 11 and delivery tube 14 and may have a diameter larger than the diameters of distal tool 11 and delivery tube 14 and large enough to abut against stop 303.

FIG. 3B illustrates a cross-sectional view of injection needle 200 in a retracted configuration according to an exemplary embodiment. As shown in FIG. 3B, distal tool 11 may be placed in a retracted position by proximally drawing flexible tube 14 until distal tool 11 no longer extends out of lumen 300. The handle assembly of injection needle 200 may also be operably coupled to flexible tube 14 and may manipulate axial movement of flexible tube 14. Accordingly, flexible tube 14 may be actuated to move in a distal direction (i.e., pushed forward) and place distal tool 11 in the extended position, as shown in FIG. 3A, and may also be actuated to retract in a proximal direction (i.e., pulled backwards) and place distal tool 11 in the retracted position. It should also be appreciated that flexible tube 14 may be actuated to place distal tool 11 in any position between the retracted position and the extended position. For example, flexible tube 14 may be slightly distally advanced to place distal tool 11 in a partially-extended position external pivoting member 218. Furthermore, it should be appreciated that one or both of flexible tube 14 and the handle assembly may include any suitable stops or limits configured to prevent proximal retraction of flexible tube 14 and thus distal tool 11 beyond a predetermined position. Moreover, in certain embodiments, the handle assembly may include any suitable locking mechanism configured to lock distal tool 11 at any axial position between and including the retracted position and the extended position.

It should also be appreciated that distal tool 11 may be comprised of a shape memory material (e.g., Nitinol) or a super elastic material such that upon extending from lumen 300, distal tool 11 may be biased to a curved or any other suitable shape, and may become substantially linear when retracted into lumen 300.

FIGS. 4A-4C illustrate another embodiment of an injection needle 400. Injection needle 400 may be substantially similar to injection needle 200 of FIGS. 2A-3B and may include flexible tube 13, distal tool 11 fluidly coupled to delivery tube 14, a clevis member 170, pivoting member 218, first control member 219, and second control member 220. As shown in FIGS. 4A-4C, however, injection needle 400 may be configured for side-folding retraction of distal tool 11.

To provide side-folding retraction for distal tool 11, each of first control member 219 and second control member 220 may be anchored by any suitable means to pivoting member 218 and may wrap around the entire circumference of pivoting member 218. In addition, first and second control members 219, 220 may be positioned on different positions relative to distal tool 11. For example, first control member 219 may be anchored to a first position of pivoting member 218 proximate a first arm 127 of clevis member 170, and second control member 220 may be anchored to a second position of pivoting member 218 proximate a second arm (not shown) of clevis member 170 and different than the first position. Accordingly, such a configuration of first control member 219 and second control member 220 may allow pivoting member 218, and thus distal tool 11, to rotate at least 180° in both the first direction and the second direction relative longitudinal axis 16. More simply, distal tool 11 may be deflected from a first position substantially aligned with longitudinal axis 16 and pointing towards a distal direction (FIG. 4A), to a second position substantially aligned with longitudinal axis 16 and pointing towards a proximal direction (FIG. 4C). In other embodiments, one or both of first control member 219 and second control member 220 may be designed to be distally advanced to cause pivoting member 218 to rotate.

Moreover, clevis member 170 may include a lumen or a slot 130 to accommodate side-folding retraction of distal tool 11. Distal tool 11 may be rotated towards slot 130 and may enter slot 130 to be housed within clevis member 170. Although not illustrated, it should be appreciated that as distal tool 11 enters slot 130 and clevis member 170, at least a portion of flexible tube 14 may exit clevis member 170 between first arm 127 and the second arm to provide space within clevis member 170 for distal tool 11. It should also be appreciated that in certain embodiments another slot may be positioned opposite slot 130 on clevis member 170 to accommodate side-folding retraction of distal tool 11 in a direction opposite from that shown in FIGS. 4A-4C.

Like the embodiments of FIGS. 2A-3B, injection needle 400 may include an appropriate handle assembly configured to effectuate actuation of first control member 219 and second control member 220. Moreover, injection needle 400 may include any suitable restriction means to regulate the range of motion of tool 11. For example, the handle assembly may include appropriate stops configured to limit the length of first control member 219 and/or second control member 220 that may be retracted. The handle assembly may also include any suitable locking mechanism configured to lock the position of distal tool 11 at the extended position shown in FIG. 4A, the side-folded retracted position shown in FIG. 4C, and any position therebetween, such as the partially-extended position shown in FIG. 4B. Furthermore, it should be appreciated that injection needle 400 may include the axial retraction and extension features of distal tool 11 and delivery tube 13 as discussed above in FIGS. 3A-3B. Moreover, injection needle 400 may include similar electrical connections and insulations as discussed above in FIGS. 2A-2C for electrically activating distal tool 11.

Figure 5A:
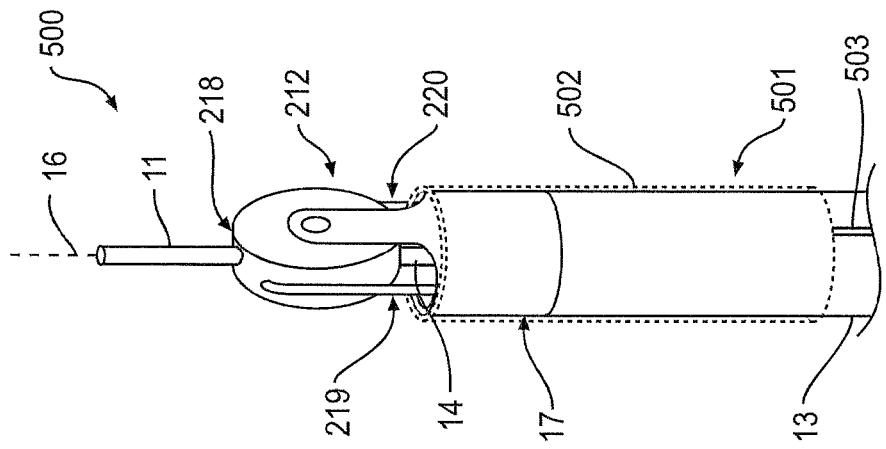
FIG. 5A illustrates a schematic view of another injection needle, according to an exemplary disclosed embodiment.
Figure 5B:
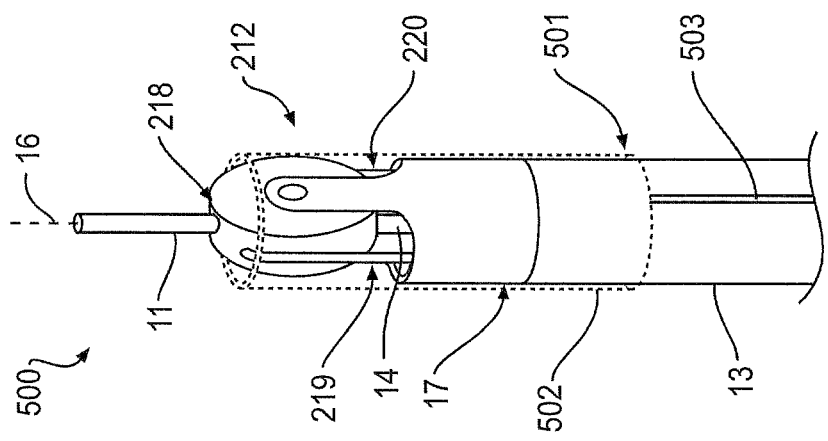
FIG. 5B illustrates a schematic view of the injection needle of FIG. 5A in a partially-retracted configuration, according to an exemplary disclosed embodiment.
Figure 5C:
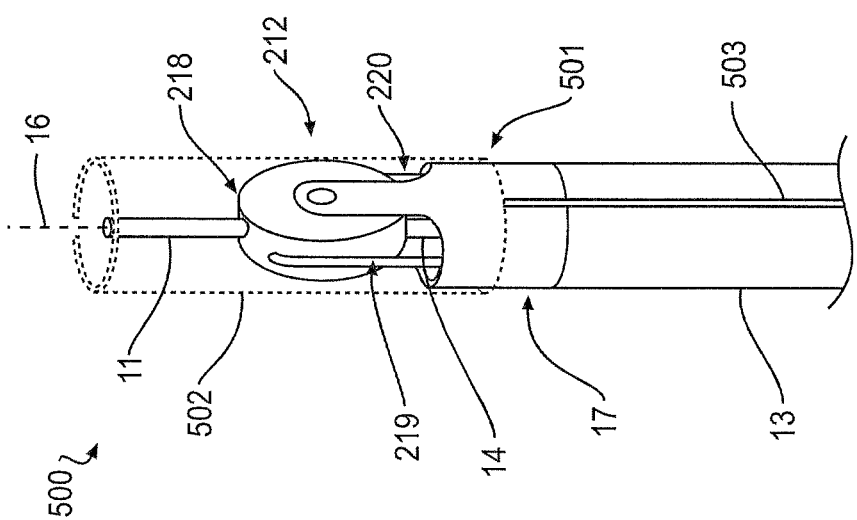
FIG. 5C illustrates a schematic view of the injection needle of FIG. 5A in a fully-retracted configuration, according to an exemplary disclosed embodiment.

FIGS. 5A-5C illustrate another injection needle 500. Injection needle 500 may be substantially similar to injection needle 200 of FIGS. 2A-3B and may include flexible tube 13, distal tool 11 fluidly coupled to delivery tube 14, clevis member 17, pivoting member 218, first control member 219, and second control member 220. As shown in FIGS. 5A-5C, injection needle 500 may further include a retractable sleeve 501 configured to selectively house and expose distal tool 11.

Retractable sleeve 501 may include a tube 502 formed of any suitable material, such as a polymeric material, and may also be reinforced with any suitable material and/or structure, such as with braiding or a coil. Tube 502 may include a channel configured to house distal tool 11 and at least a portion of positioning mechanism 212. For example, in a fully-extended configuration shown in FIG. 5A, tube 502 may completely cover distal tool 11 and pivoting member 218, and partially cover clevis member 17. It should be appreciated, however, that tube 502 may be any appropriate size to house any other elements of injection needle 500. For example, tube 502 may have a suitable length to cover a portion of flexible tube 13 and completely cover distal tool 11, pivoting member 218, and clevis member 17.

Retractable sleeve 501 may also include one or more actuation members 503 operably coupled to tube 502 by any suitable attachment or fastening means. One or more actuation members 503 may include any suitable coupling device such as, for example, a wire, a rod, or a hollow tube. One or more actuation members 503 may be configured to effectuate axial movement of tube 502 relative to longitudinal axis 16. For example, and as shown in FIG. 5A, retractable sleeve 501 may be placed in an extended position to house distal tool 11 and a portion of positioning mechanism 212 by pushing forward one or more actuation members 503, thereby distally advancing tube 502 over positioning mechanism 212 and distal tool 11. As shown in FIG. 5B, retractable sleeve 501 may be in a partially-retracted position to expose distal tool 11 and partially house positioning mechanism 212 by pulling back one or more actuation members 503, thereby proximally retracting tube 502 and uncovering distal tool 11. In the partially-retracted position, distal tool 11 may be exposed to provide the appropriate treatment to target issue; however, positioning mechanism 212 may be restricted from fully deflecting distal tool 11 by being housed within and bound by tube 502. As shown in FIG. 5C, retractable sleeve 501 may be in a fully-retracted position to expose both distal tool 11 and positioning mechanism 212 by further pulling back one or more actuation members 503 and retracting tube 502. In the fully-retracted position, distal tool 11 may be exposed to provide the appropriate treatment to target issue, and positioning mechanism 212 may be allowed to fully deflect distal tool 11 relative to longitudinal axis 16. It should be appreciated that one or more actuation members 503 may be external of flexible tube 13 for all or a portion of tube 13. For example, one or more actuation members 503 may enter the channel of tube 13 near the distal end of tube 13 and extend proximally.

Like the embodiments of FIGS. 2A-4C, injection needle 500 may include an appropriate handle assembly configured to effectuate actuation of first control member 219 and second control member 220. Moreover, injection needle 500 may include any suitable restriction means to regulate the axial movement of retractable sleeve 501. For example, appropriate stops may be positioned within positioning mechanism 212. The handle assembly may also include appropriate stops configured to limit the length of one or more actuation members 503 that may be proximally retracted and distally advanced. The handle assembly may also include any suitable locking mechanism configured to lock the position of retractable sleeve 501. For example, the locking mechanism may fix tube 502 at the fully-extended position shown in FIG. 5A, the fully-retracted position shown in FIG. 5C, and any position therebetween, such as the partially-retracted position shown in FIG. 5B. Furthermore, it should also be appreciated that injection needle 500 may include the axial retraction and extension features of distal tool 11 as discussed above in FIGS. 3A-3B. Moreover, injection needle 500 may include similar electrical connections and insulations as discussed above in FIGS. 2A-2C for electrically activating distal tool 11.

Accordingly, by retracting distal tool 11, as disclosed in FIGS. 3A-4C, and covering distal tool 11 with retractable sleeve 501, as disclosed in FIGS. 3A-5C, injection needle 200, 400, 500 may be delivered through at least one working channel 6 of endoscope 1 and avoid skiving the walls of channel 6 with distal tool 11. Thus, damage to both distal tool 11 and endoscope 1 may be minimized. In addition, retracting and covering distal tool 11 may also prevent inadvertent damage to tissue as injection needle 200, 400, 500 is delivered to and/or removed from body anatomies.

It should also be appreciated that the extendable and retractable features of distal tool 11 disclosed in FIGS. 3A-4C and the retractable sleeve 501 disclosed in FIGS. 5A-5C may be employed with any other suitable medical device having a positioning mechanism configured to deflect a distal tool, such as, for example, any of the medical devices disclosed in U.S. Provisional Application No. 61/553,301, which is incorporated herein by reference in its entirety.

As alluded to above, although distal tool 11 in FIGS. 2A-5C may embody an electrically conductive tube or needle, it should be appreciated that the distal tool of the present disclosure may include any other suitable treatment instrument for a medical procedure. For example, the distal tool may comprise a cutting mechanism, as shown in FIGS. 6A-6C.

Figure 6C:
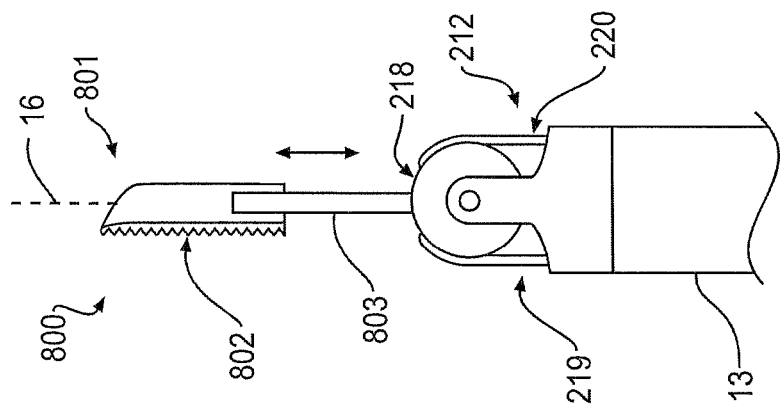
FIG. 6C illustrates a schematic view of another medical device, according to an exemplary disclosed embodiment.
Figure 6B:
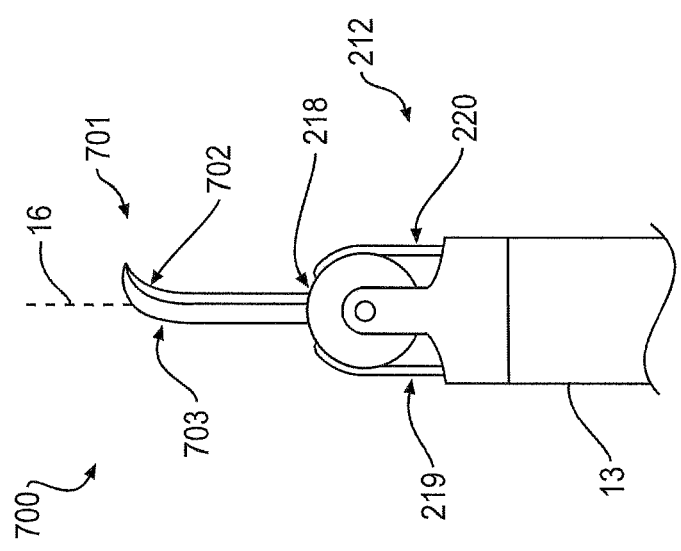
FIG. 6B illustrates a schematic view of another medical device, according to an exemplary disclosed embodiment.
Figure 6A:
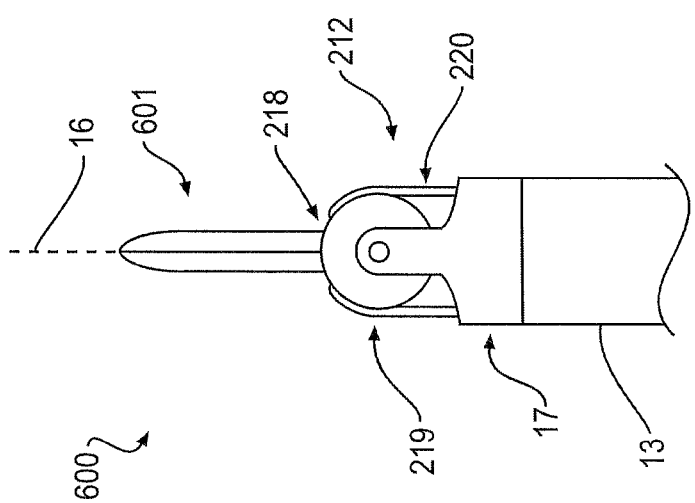
FIG. 6A illustrates a schematic view of a medical device, according to an exemplary disclosed embodiment.

FIG. 6A illustrates a medical device 600 according to an exemplary embodiment. Similar to injection needle 200 of FIGS. 2A-2C, medical device 600 may comprise flexible tube 13 and positioning mechanism 212 including clevis member 17, pivoting member 218, first control member 219, and second control member 220. In addition, medical device 600 may include a distal tool 601 operably coupled to positioning mechanism 212. As shown in FIG. 6A, distal tool 601 may comprise a double-edged blade configured to cut and dissect tissue. More particularly, first control member 219 or second control member 220 may be retracted to cause pivoting member 218 to rotate and deflect distal tool 601. Deflecting distal tool 601 may create a cutting action against targeted tissue in the first direction and the second direction relative to longitudinal axis 16. Such deflecting cutting action may provide a quicker and simplified method to dissect tissue.

FIG. 6B illustrates another medical device 700 according to an exemplary embodiment. Medical device 700 may be similar to medical device 600 of FIG. 6A. As shown in FIG. 6B, however, a distal tool 701 may be a curved blade and may include a concave portion 702 having a sharp edge configured to cut tissue and a convex portion 703 having a dull edge configured to prevent cutting of tissue. Such a configuration provides cutting of tissue in only one direction. In other words, as distal tool 701 is deflected by actuation of first and second control members 219, 220, distal tool 701 may only cut tissue facing concave portion 702. Thus, tissue may be cut and dissected when distal tool 701 is deflected towards tissue facing concave portion 702, but when distal tool 701 is deflected in the opposite direction, tissue contacting convex portion 703 may not be cut and dissected due to its dull edge. Distal tool 701 may therefore provide a safer and more precise device for dissecting tissue. It should be appreciated, however, that both concave portion 702 and convex portion 703 may include a sharp edge for cutting tissue.

FIG. 6C illustrates another medical device 800 according to an exemplary embodiment. Medical device 800 may be similar to medical device 600, 700 of FIGS. 6A-6B. As shown in FIG. 6C, however, a distal tool 801 may be a serrated blade including a serrated edge 802 and may be configured for axial translation relative to longitudinal axis 16 to effectuate a sawing action to cut and dissect tissue. Such a sawing action may ease dissection of, for example, harder and thicker types of tissue. Distal tool 801 may also be deflected to opposite sides of longitudinal axis 16 by actuation of first and second control members 219, 220 in a similar manner as in FIGS. 6A-6B.

A control element 803 may be coupled to distal tool 801 and may run through lumen 300 (not shown in FIG. 6C) defined within pivoting member 218. To actuate axial translation of distal tool 801 (as indicated by the double-headed arrow), control element 803 may be distally advanced or proximally retracted through lumen 300 of pivoting member 218 and the channel of flexible tube 13. Control element 803 may be any suitable coupling device configured to provide axial translation of distal tool 801, such as, for example, a wire, a rod, or a hollow tube. Control element 803 may also be flexible to accommodate bending and deflection of control element 803 upon rotation of pivoting member 218.

Furthermore, medical device 600, 700, 800 may include the extendable and retractable features disclosed in FIGS. 3A-3B, the extendable and side-folding retraction features disclosed in FIGS. 4A-4C, and/or the retractable sleeve 501 disclosed in FIGS. 5A-5C. That is, distal tool 601, 701, 801 may axially extend and retract relative to pivoting member 218 in a similar manner as distal tool 11 of FIGS. 3A-3B, may extend and retract into a slot of clevis member 17 upon rotation of pivoting member 218 in a similar manner as distal tool 11 of FIGS. 4A-4C, and/or may be exposed and housed within retractable sleeve 501 upon axial movement of retractable sleeve 501 in a similar manner as distal tool 11 of FIGS. 5A-5C.

Similar to injection needle 200 of FIGS. 2A-5C, an appropriate handle assembly (not shown) may be operably coupled to first control member 219 and second control member 220 of medical device 600, 700, 800. In addition, the handle assembly may include an appropriate locking mechanism to lock distal tool 601, 701, 801 in any suitable position. For example, the locking mechanism may secure distal tool 601, 701, 801 in a deflected position, and may release distal tool 601, 701, 801 from the deflected position when desired. It should be appreciated that medical device 800 may include any suitable restriction means to regulate the axial translation of distal tool 801. For example, the handle assembly may include appropriate stops configured to limit the length of control element 803 that may be extended and retracted. Additionally, or alternatively, a portion of control element 803 may include a width that may be bound by stop 303 of lumen 300, as described above in FIGS. 3A-3B.

Although not shown in FIGS. 6A-6B, it should be appreciated that flexible tube 14 may be fluidly coupled to distal tool 601 and distal tool 701 in a similar manner as disclosed in FIGS. 2A-2C. In such a configuration, distal tool 601 and distal tool 701 may be hollow and may include an opening (not shown) along any desired location of distal tool 601 and distal tool 701, such as, for example, the tip. Accordingly, a suitable fluid may be delivered from a fluid source (not shown), through delivery tube 14, and out of the opening of distal tool 601 and distal tool 701.

Distal tool 601, 701, 801 may also comprise any material capable of conducting electricity, such as, for example, stainless steel, nickel titanium alloys, and the like. In addition, and similar to the embodiments of FIGS. 2A-2C, one or both of first control member 219 and second control member 220 may provide an electrical pathway from a source of electrical current (not shown) to distal tool 601, 701, 801. Moreover, one or more separate conductive wires, cables, sheaths, or the like may be twisted along, adjacent to, formed within, or physically separated from one or both of first control member 219 and second control member 220 and may provide the electrical pathway to distal tool 11. Additionally, or alternatively, delivery tube 14 may provide an electrical pathway from the source of electrical current to distal tool 601 and distal tool 701, in a similar manner as the embodiments of FIGS. 2A-2C, and control element 803 may provide an electrical pathway from the source of electrical current to distal tool 801 in a similar manner as delivery tube 14. Accordingly, distal tool 601, 701, 801 may coagulate, cauterize, dissect, burn, and/or cut target tissue upon being energized by an electrical current. Moreover, distal tool 11 may be configured to perform monopolar or bipolar cauterization.

In FIG. 6B, convex portion 703 of distal tool 701 may be coated with an appropriate insulating material. For example, an insulating sheath may cover convex portion 703, or convex portion 703 may be powder coated with an insulating material. Therefore, tissue contacting convex portion 703 of distal tool 701 may be protected from cauterization and damage when distal tool 701 is electrically energized.

It should also be appreciated that medical device 600, 700, 800 may include any other suitable positioning mechanism configured to deflect distal tool 601, 701, 801. For example, medical device 600, 700, 800 may include any of the positioning mechanisms disclosed in U.S. Provisional Application No. 61/553,301.

In certain other embodiments, the distal tool may serve as a guide for other endoscopic tools inserted into body anatomies. For example, an electrocautery loop may be fed through an insertion tube coupled to the distal tool. The electrocautery loop may then exit the distal tool to reach target tissue. By actuating the positioning mechanism, the distal tool, and thus the electrocautery loop, may be deflected to a desired position. Any other device may be delivered through the distal tool including, as examples, snares, baskets, brushes, needles, forceps, graspers, ablation needles, and the like. Moreover, any device delivered through distal tool may include its own independent steering mechanism.

Moreover, it should be appreciated that any of devices 200, 400, 500, 600, 700, and 800 may include an imaging system for visualizing the body anatomies. The imaging system may include any suitable system for capturing images within body anatomies, such as, for example, an optical fiber and/or an electronic camera including illumination units. Accordingly, devices 200, 400, 500, 600, 700, and 800 may then be used without endoscope 1 for visualization purposes. Nevertheless, employing devices 200, 400, 500, 600, 700, and 800 having an imaging system with endoscope 1 may provide multiple areas of visualization, including one area from endoscope 1 and another area from devices 200, 400, 500, 600, 700, and 800.

It should also be appreciated that in any of the above embodiments, distal tool 11 may be sharp or may be dull, and may include any suitable cross-sectional shape, such as, for example, an oval shape, a rectangular shape, a triangular shape, or a circular shape. Moreover, in certain embodiments, positioning mechanism 212 may include a single control member configured to rotate pivoting member 218 upon actuation. Positioning mechanism 212 may also include a suitable biasing member (not shown), such as a spring, to bias pivoting member 218 in a desired orientation. For example, the biasing member may bias pivoting member 218 such that distal tool 11 may be offset from longitudinal axis 16.

Figure 7A:
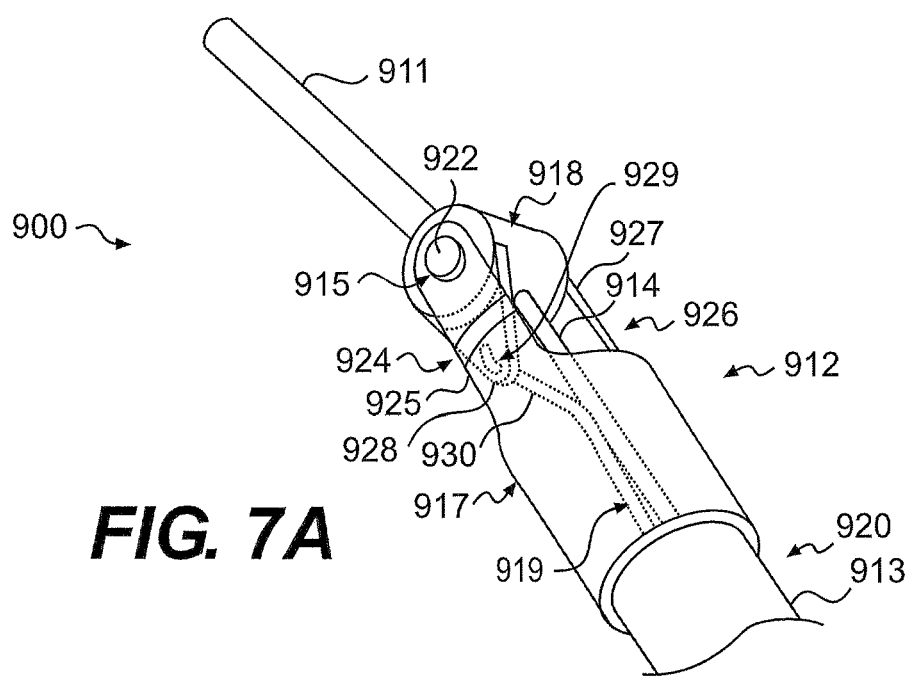
FIG. 7A illustrates a schematic view of a suction device, according to an exemplary disclosed embodiment.
Figure 7B:
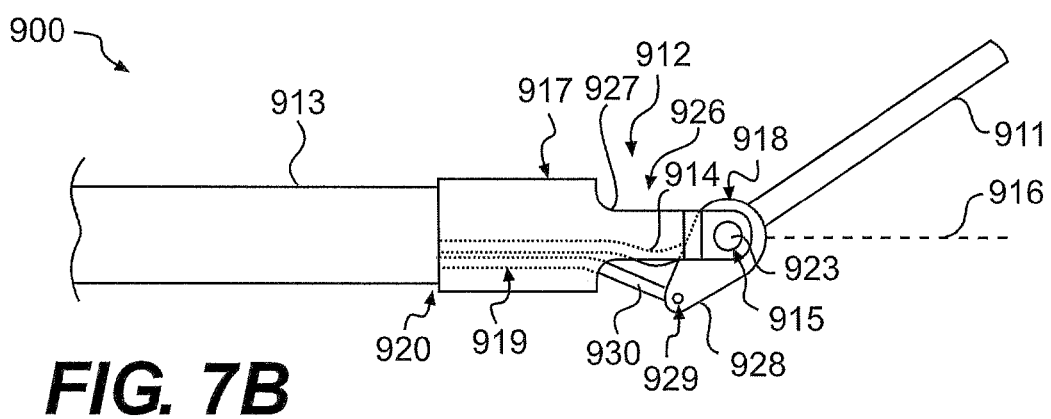
FIG. 7B illustrates another schematic view of the suction device of FIG. 7A, according to an exemplary disclosed embodiment.
Figure 7C:
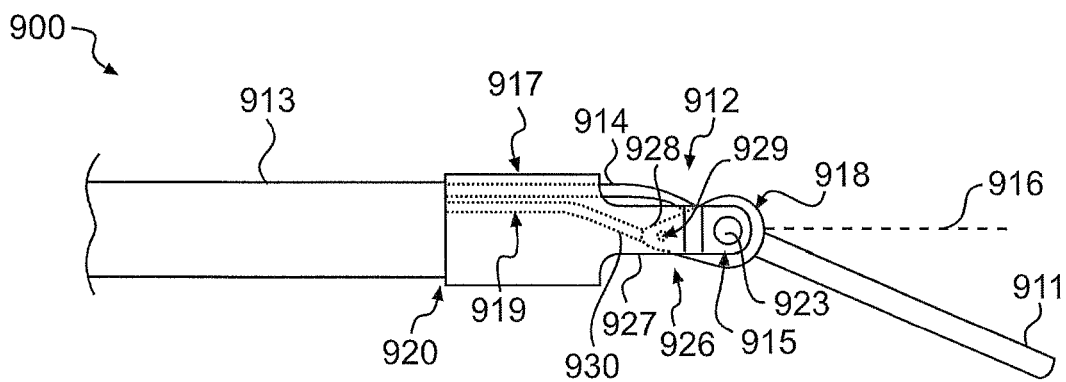
FIG. 7C illustrates another schematic view of the suction device of FIG. 7A, according to an exemplary disclosed embodiment.

FIGS. 7A-7C illustrate a suction device 900 according to an exemplary disclosed embodiment. Suction device 900 may extend through the at least one working channel 6 of endoscope 1 and exit opening 7 to reach a desired treatment location. Suction device 900 may be configured to, for example, provide suction for grasping and/or retracting tissue and/or removing debris and fluids.

As illustrated in FIG. 7A, suction device 900 may include a distal tool 911, a positioning mechanism 912, and a flexible tube 913. Distal tool 911 may be hollow and include a lumen fluidly coupled to a suction tube 914 extending through flexible tube 913. In some embodiments, distal tool 911 may be a hypotube. A vacuum may be applied from a vacuum source (not shown), through suction tube 914, and through a distal opening of distal tool 911. Distal tool 911 may be formed of any suitable material configured to support suction therethrough, such as, for example, stainless steel, nickel titanium alloys, polymeric materials, plastics, combinations of such materials, and the like. A distal end of distal tool 911 may be relatively blunt and may be configured to form a fluid-tight seal against targeted tissue upon application of the vacuum. Moreover, by being relatively blunt, suction device 900 may be advanced through the at least one working channel 6 of endoscope 1 without scraping or damaging the walls of channel 6. A proximal end of distal tool 911 may be operably coupled to positioning mechanism 912.

Positioning mechanism 912 may be configured to rotate, or deflect, distal tool 911 of suction device 900 around a pivot 915. Therefore, distal tool 911 may be connected to flexible tube 913 near pivot 915. In other words, and as show in FIGS. 7B-7C, distal tool 911 may pivot in a lateral direction relative to a longitudinal axis 916 of flexible tube 913 by actuation of positioning mechanism 912. Positioning mechanism 912 may include a clevis member 917, a pivoting member 918, and a control member 919. Control member 919 may include any suitable coupling device, such as, for example, a wire, a rod, a filament, or a hollow tube.

Clevis member 917 may be disposed on a distal end 20 of flexible tube 913. A proximal portion of clevis member 917 may be positioned over flexible tube 913 and may be hollow to provide communication between flexible tube 913 and pivoting member 918. Alternatively, the proximal portion of clevis member 917 may be under (or within) flexible tube 913, or abut against flexible tube 913.

In some embodiments, pivoting member 918 may be positioned within clevis member 917 and may be coupled to clevis member 917 via a first pin (or boss) 922 and a second pin (or boss) 923. First pin 922 may extend from a first side 924 of pivoting member 918 and may rotatably connect pivoting member 918 to a first arm 925 of clevis member 917. Second pin 923 may extend from a second side 926 of pivoting member 918 and may rotatably connect pivoting member 918 to a second arm 927 of clevis member 917. Accordingly, pivoting member 918 may be configured to rotate about first pin 922 and second pin 923. In certain embodiments, pivoting member 918 may be coupled to clevis member 917 via a suitable hinge (or living hinge) to effectuate deflection of pivoting member 918 relative to clevis member 917. Pivoting member 918 may include a lumen extending to distal tool 911. The lumen may be fluidly coupled to distal tool 911 such that suction or infusion may be provided to distal tool 911. In one example, suction tube 914 may partially extend through the lumen of pivoting member 918 and may be fluidly coupled to distal tool 911. In certain other embodiments, suction tube 914 may extend through the lumen and may be directly connected to distal tool 911 by any suitable means, such as, for example, adhesives, welding, friction fit, crimping, and the like. Alternatively, suction tube 914 and distal tool 911 may be integrally formed, in which distal tool 911 may be a rigid extension of suction tube 914. In another example, suction tube 914 may terminate on an exterior surface of pivoting member 918 and may be fluidly coupled to a proximal opening of the lumen. Accordingly, a vacuum force may travel through the distal opening of distal tool 911 and through the lumen of pivoting member 918 and into suction tube 914. Suction tube 914 may be formed of any suitable flexible material to accommodate bending and deflection of suction tube 914 upon rotation of pivoting member 918. Suction tube 914 may be composed of one or more of metals, plastics, polymers, and elastomers, and may be formed of multiple materials to vary the flexibility and the stiffness along suction tube 914. In certain embodiments, a distal portion of suction tube 914 may be more flexible then a proximal portion of suction tube 914 to accommodate bending. For example, the distal portion of suction tube 914 may be formed of a spring or coil, such as a metallic spring or coil, covered by a flexible material, such as a polymeric sheath, and the proximal portion of suction tube 914 may be formed of a stiff, polymeric tube. It should also be appreciated that the suction tube 914 may vary in stiffness/flexibility by, for example, varying a wall thickness of suction tube 914, varying a material hardness of suction tube 914, forming suction tube 914 of stiffer and more flexible materials along suction tube 914, and cutting out holes and/or notches in the wall of suction tube 914.

Pivoting member 918 may also include a proximally extending coupling element in the form of a tang 928. Tang 928 and control member 919 may be positioned proximate first side 924, or alternatively second side 926, of pivoting member 918 to provide a substantially central access for suction tube 914 to distal tool 911. Tang 928 may be, for example, a fin-shaped protrusion coupled to control member 919 at a coupling point 929. Tang 928 may also include any suitable length. Coupling point 929 between control member 919 and tang 928 may be any suitable pivoting arrangement with any suitable geometry, and may be on positioned on any suitable position of tang 928. For example, control member 919 may extend through a hole on a side surface of tang 928 and may be crimped to secure member 919 to tang 928. The hole may have a diameter larger than the diameter of member 919 to allow suitable rotation of member 919 within the hole. Accordingly, as control member 919 is pushed forward (FIG. 7B) or pulled back (FIG. 7C), control member 919 and coupling member 928 may pivot relative to one another at coupling point 929.

As will be discussed further below, a suitable handle assembly may be operably coupled to control member 919 external endoscope 1 and may manipulate control member 919. Control member 919 may be actuated to advance in a distal direction, as shown in FIG. 7B. In other words, control member 919 may be pushed forward, causing control member 919 to pivot relative to tang 928 and rotate pivoting member 918, resulting in the deflection of distal tool 911 in a first direction. As shown in FIG. 7C, control member 919 may be retracted in a proximal direction (i.e., pulled backward), causing control member 919 to pivot relative to tang 928 and rotate pivoting member 918 in the opposite direction, resulting in the deflection of distal tool 911 in a second direction opposite the first direction. Therefore, an angle between distal tool 911 and longitudinal axis 916 may be altered upon actuation of control member 919. Deflection of distal tool 911, if desired, may be restricted through any number of suitable stop structures. For example, one or more of flexible tube 913, clevis member 917, control member 919, tang 928, and coupling point 929 may be dimensioned such that control member 919 abuts against either clevis member 917 or the internal wall of flexible tube 913 when distal tool 911 reaches predetermined angles relative to longitudinal axis 916.

Control member 919 may also include a bent portion 930. FIG. 7B illustrates that as control member 919 is distally advanced, bent portion 930 may extend external clevis member 917 at an angle offset from longitudinal axis 916, while the portion of control member 919 proximal bent portion 930 moves towards the internal wall of flexible tube 913. Because control member 919 may pivot relative to tang 928, and bent portion 930 may extend from clevis member 917 at an angle, tang 928 may in turn significantly deflect out of the slot defined between first and second arms 925, 927 of clevis member 917. Therefore, pivoting member 918 may have an increased angular rotation, allowing distal tool 911 to have a greater range of motion when control member 919 is distally advanced.

The bent portion 930 may also restrict the range of motion of distal tool 911 when control member 919 is proximally retracted. As shown in FIG. 7C, when control member 919 is proximally retracted, control member 919 may pivot relative to tang 928, and bent portion 930 may be retracted into clevis member 917. Bent portion 930, however, may restrict tang 928 from movement outside of the slot defined between first and second arms 925, 927. Pivoting member 918 may therefore have a decreased angular rotation, and thus distal tool 911 may have a smaller range of motion when control member 919 is proximally retracted relative to when control member 919 is distally advanced.

Accordingly, as the bend of control member 919 becomes larger (i.e., the bend angle between bent portion 930 and the rest of control member 919 becomes smaller), the range of motion of distal tool 911 when control member 919 is distally advanced may become greater, but the range of motion of distal tool 911 when control member 919 is proximally retracted may become smaller. Such a configuration may have certain advantages. For example, it may be beneficial for distal tool 911 to have an increased range of motion in one direction to reach targeted tissue for suction, while limiting the range of motion in the opposite direction to prevent distal tool 911 from contacting and damaging healthy tissue. Furthermore, the arrangement of tang 928 with bent portion 930 provides a collapsed and compact configuration for positioning mechanism 912. That is, substantial portions of control member 919 and tang 928 may be housed within clevis member 917, thereby preventing, for example, undesired snagging of tissue. It should also be appreciated that by increasing the length of bent portion 930, the range of motion when control member 919 is distally advanced may become greater, and the range of motion of distal tool 911 when control member 919 is proximally retracted may become smaller. In addition, varying the flexibility of bent portion 930 may affect the range of motion of distal tool 911. For example, forming bent portion 930 of a more flexible material relative to the rest of control member 919 may allow bent portion 930 to bend or deflect as control member 919 is proximally retracted and distally advanced. Therefore, increasing the flexibility of bent portion 930 may increase the range of motion of distal tool 911 when control member 919 is both proximally retracted and distally advanced.

Figure 8A:
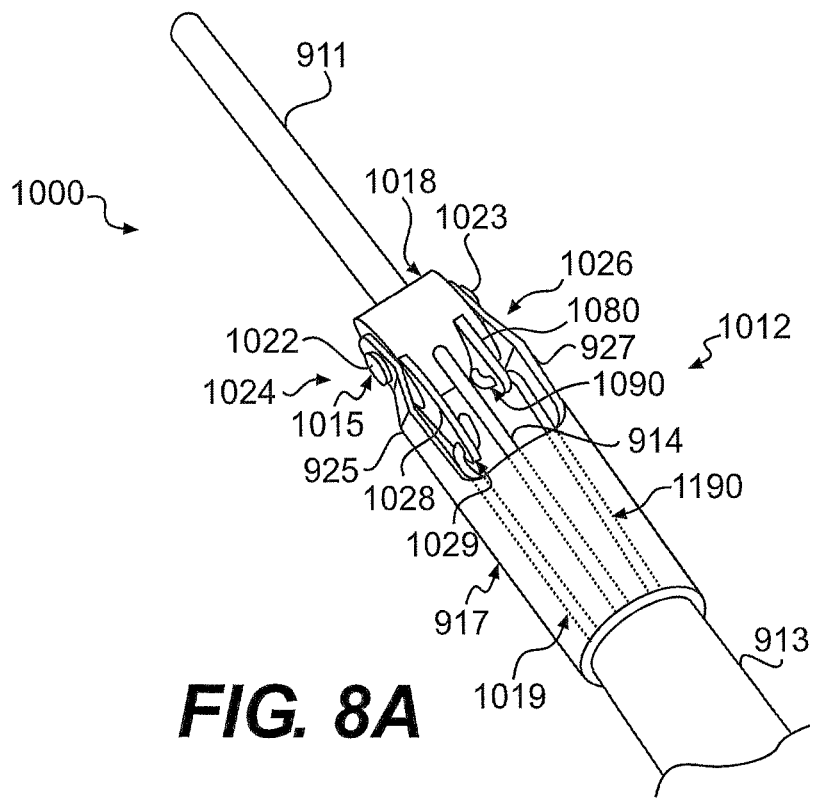
FIG. 8A illustrates a schematic view of another suction device, according to an exemplary disclosed embodiment.
Figure 8B:
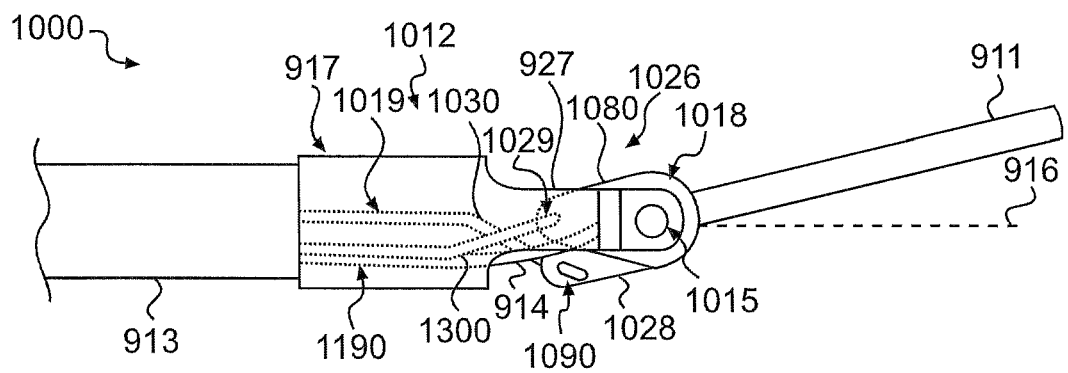
FIG. 8B illustrates another schematic view of the suction device of FIG. 8A, according to an exemplary disclosed embodiment.
Figure 8C:
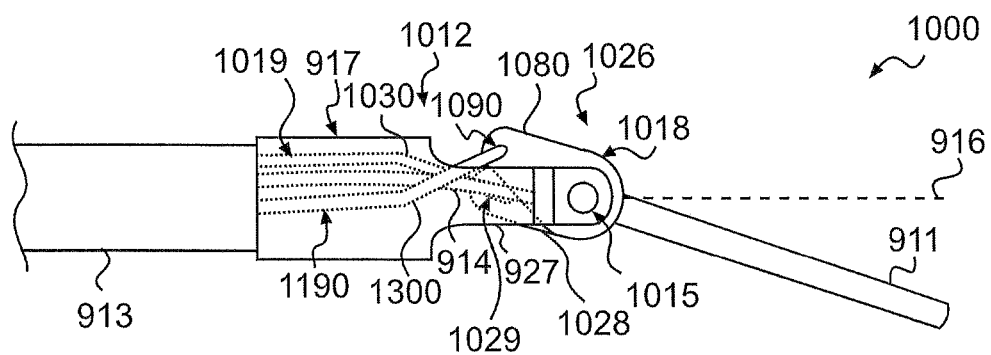
FIG. 8C illustrates another schematic view of the suction device of FIG. 8A, according to an exemplary disclosed embodiment.

FIGS. 8A-8C illustrate another embodiment of a suction device 1000. Similar to the embodiments of FIGS. 7A-7C, suction device 1000 may include a flexible tube 913 and a distal tool 911 fluidly coupled to suction tube 914. Suction device 1000 may also include a positioning mechanism 1012 configured to deflect distal tool 911 around a pivot 1015. Therefore, distal tool 911 may be connected to flexible tube 913 near pivot 1015. Similar to the embodiments of FIGS. 7A-7C, positioning mechanism 1012 may include clevis member 917. In addition, positioning mechanism 1012 may include a pivoting member 1018, a first control member 1019, and a second control member 1190. Like control member 919, first and second control members 1019, 1190 may include any suitable coupling device, such as, for example, a wire, a rod, a filament, or a hollow tube.

Pivoting member 1018 may be positioned within clevis member 917 and coupled to clevis member 917 via a first pin (or boss) 1022 and a second pin (or boss) 1023. First pin 1022 may extend from a first side 1024 of pivoting member 1018 and may rotatably connect pivoting member 1018 to first arm 925 of clevis member 917. Second pin 1023 may extend from a second side 1026 of pivoting member 1018 and may rotatably connect pivoting member 1018 to second arm 927 of clevis member 917. Accordingly, pivoting member 1018 may be configured to rotate about first pin 1022 and second pin 1023. Suction tube 914 may be fluidly coupled to distal tool 911, similar to the embodiments of FIGS. 7A-7C.

Pivoting member 1018 may also include a first coupling element in the form of a tang 1028 proximate first pin 1022 and a second coupling element in the form of a tang 1080 proximate second pin 1023. Suction tube 914 may be fluidly coupled to distal tool 911 between tangs 1028, 1080. Tangs 1028, 1080 may be, for example, fin-shaped protrusions. In addition, tangs 1028, 1080 may be symmetrically or asymmetrically disposed about pivoting member 1018 and symmetrically or asymmetrically disposed on pivoting member 1018 along pivot 1015. Furthermore, tangs 1028, 1080 may include any suitable length. Tang 1028 may be coupled to first control member 1019 at a first coupling point 1029, and tang 1080 may be coupled to second control member 1190 at a second coupling point 1090. First and second coupling points 1029, 1090 may be any suitable pivoting arrangement with any suitable geometry and may be positioned on any suitable position of tangs 1028, 1080. Accordingly, as first control member 1019 is pushed forward (FIG. 8B) or pulled back (FIG. 8C), first control member 1019 and tang 1028 may pivot relative to one another at first coupling point 1029. Moreover, as second control member 1190 is pushed forward (FIG. 8C) or pulled back (FIG. 8B), second control member 1190 and second control element 1080 may pivot relative to one another at second coupling point 1090.

An appropriate handle assembly (not shown) may be connected to first control member 1019 and second control member 1190 and may manipulate first and second control members 1019, 1190. The handle may be, for example, associated with endoscope 1. As shown in FIG. 8B, the handle assembly may be actuated to advance first control member 1019 in a distal direction, while simultaneously retracting second control member 1190 in a proximal direction. That is, first control member 1019 may be pushed forward, and second control member 1190 may be pulled back, causing first and second control members 1019, 1190 to pivot relative to tangs 1028, 1080, respectively, and rotate pivoting member 1018, resulting in the deflection of distal tool 911 in a first direction.

As shown in FIG. 8C, the handle assembly may be actuated to retract first control member 1019 in a proximal direction, while simultaneously advancing second control member 1190 in a distal direction. In other words, first control member 1019 may be pulled back, and second control member 1190 pushed forward, causing first and second control members 1019, 1190 to pivot relative to tangs 1028, 1080, respectively, and rotate pivoting member 1018, resulting in the deflection of distal tool 911 in a second direction opposite the first direction. Thus, an angle between distal tool 911 and the longitudinal axis 916 of flexible tube 913 may be altered upon actuation of first and second control members 1019, 1190. Deflection of distal tool 911, however, may be restricted once either of first control member 1019 or second control member 1190 abuts against clevis member 917 or the internal wall of flexible tube 913. In certain embodiments, one or more of tang 1028, tang 1080, and clevis member 917 may include a protrusion or the like to limit rotational movement of pivoting member 1018 by, for example, abutting against clevis member 917 or tangs 1028, 1080. It should be appreciated that the pushing/pulling of first control member 1019 and the pushing/pulling of second control member 1190 may be effectuated simultaneously or one of the first and second control member 1019 and 1190 may be passively pushed/pulled after effectuation of the other.

First control member 1019 may include a bent portion 1030, and second control member 1190 may include a bent portion 1300. As shown in FIGS. 8B and 8C, bent portion 1030 and bent portion 1300 may point in opposite directions. Moreover, the bend angle between bent portion 1030 and the rest of first control member 1019 may be substantially the same as the bend angle between bent portion 1300 and the rest of second control member 1190. In addition, tang 1028 and tang 1080 may have a staggered configuration, wherein, when distal tool 911 is substantially aligned with longitudinal axis 916, tang 1028 (and particularly its coupling point 1029) may be on one side of longitudinal axis 916 (e.g., above longitudinal axis 916), and tang 1080 (and particularly its coupling point 1090) may be on the other side of longitudinal axis 916 opposite tang 1028 (e.g., below longitudinal axis 916). Such a staggered configuration may accommodate the opposite directions to which bent portion 1030 and bent portion 1300 extend. As such, the range of motion when distal tool 911 is deflected in the first direction is substantially the same as the range of motion when distal tool 911 is deflected in the second direction. Moreover, in certain embodiments, distal tool 911 may be deflected as much as 90 degrees relative to longitudinal axis 916 in either direction. It should also be appreciated that tangs 1028, 1080 may be any suitable shape to increase or decrease the leverage of first and second control members 1019, 1190 in rotating pivoting member 1018. For example, a long and thin shape of tangs 1028, 1080 may increase the leverage of first and second control members 1019, 1190. In addition, the position and/or the strength of connection points 1029, 1090 may increase or decrease the leverage of first and second control members 1019, 1190 in rotating pivoting member 1018. In some embodiments, tang 1028 and tang 1080 may have different lengths.

Such a configuration may have certain advantages. For example, because the range of motion of distal tool 911 may be large and substantially the same in both directions of deflection, distal tool 911 may have increased maneuverability, which may be advantageous when manipulating suction device 1000 in tortuous anatomies of the body. In addition, the increased maneuverability of distal tool 911 allows a greater area of tissue on both sides of distal tool 911 to be treated and reached for suction. Furthermore, and similar to the embodiments of FIGS. 7A-7C, the arrangement of tangs 1028, 1080 with bent portions 1030, 1300 provides a collapsed and compact configuration for positioning mechanism 1012.

Figure 9A:
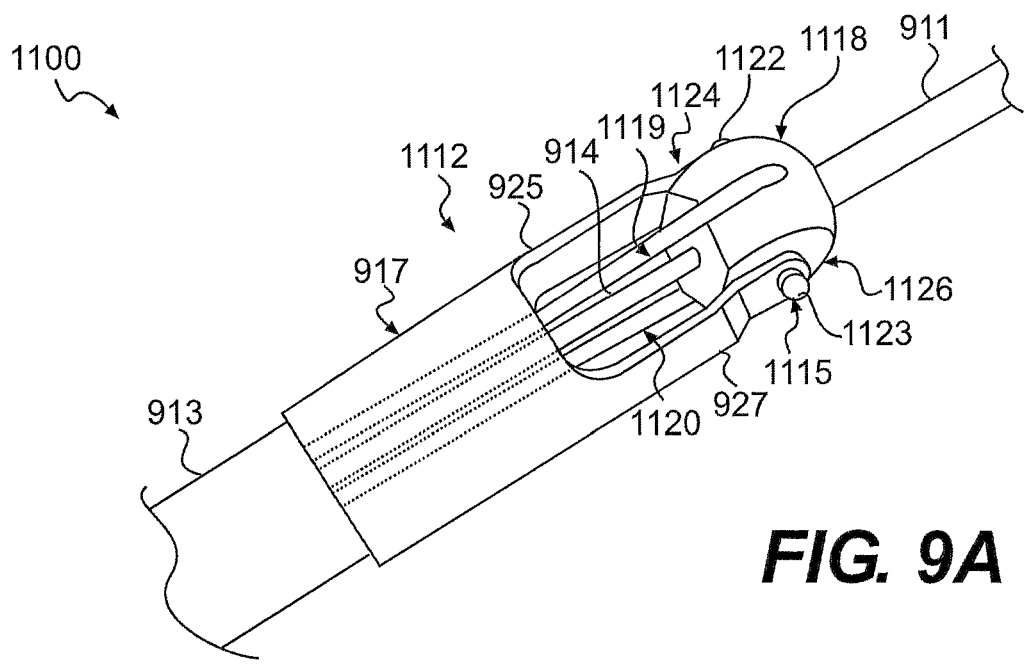
FIG. 9A illustrates a schematic view of another suction device, according to an exemplary disclosed embodiment.
Figure 9B:
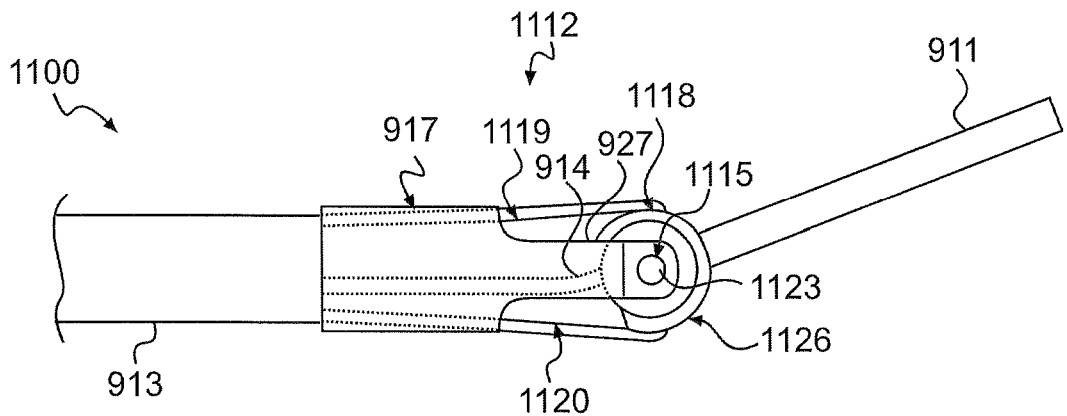
FIG. 9B illustrates another schematic view of the suction device of FIG. 9A, according to an exemplary disclosed embodiment.
Figure 9C:
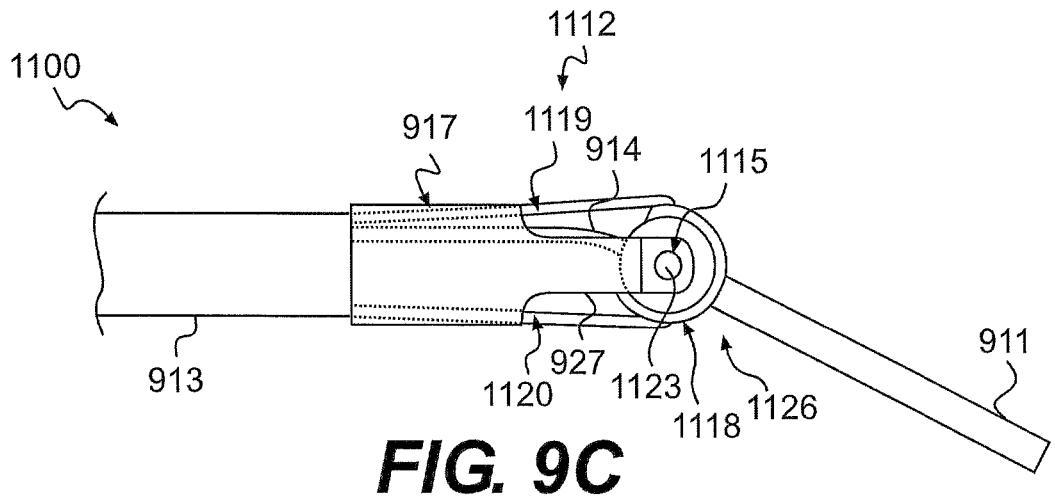
FIG. 9C illustrates another schematic view of the suction device of FIG. 9A, according to an exemplary disclosed embodiment.

FIGS. 9A-9C illustrate another embodiment of a suction device 1100. Similar to the embodiments of FIGS. 7A-8C, suction device 1100 may include flexible tube 913 and distal tool 911 fluidly coupled to suction tube 914. Suction device 1100 may also include a positioning mechanism 1112 configured to deflect distal tool 911 around a pivot 1115. Therefore, distal tool 911 may be connected to flexible tube 913 near pivot 1115. Similar to the embodiments of FIGS. 7A-8C, positioning mechanism 1112 may include clevis member 917. In addition, positioning mechanism 1112 may include a pivoting member 1118, a first control member 1119, and a second control member 1120. Like control member 919 and first and second control members 1019, 1190, first and second control members 1119, 1120 may include any suitable coupling device, such as, for example, a wire, a rod, a filament, or a hollow tube.

Pivoting member 1118 may be positioned within clevis member 917 and coupled to clevis member 917 via a first pin (or boss) 1122 and a second pin (or boss) 1123. First pin 1122 may extend from a first side 1124 of pivoting member 1118 and may rotatably connect pivoting member 1118 to first arm 925 of clevis member 917. Second pin 1123 may extend from a second side 1126 of pivoting member 1118 and may rotatably connect pivoting member 1118 to second arm 927 of clevis member 917. Accordingly, pivoting member 1118 may be a configured to rotate about first pin 1122 and second pin 1123.

A distal portion of first control member 1119 may be anchored to pivoting member 1118 on a first surface of pivoting member 1118, and a distal portion of second control member 1120 may be anchored to pivoting member 1118 on a second surface opposite the first surface of pivoting member 1118. First and second control members 1119, 1120 may be anchored to pivoting member 1118 by any suitable means, such as, for example, adhesives, welding, crimping, fasteners, and the like. Moreover, first and second control members 1119, 1120 may be substantially aligned with each other and may be positioned on opposite sides of distal tool 911. In addition, suction tube 914 may be fluidly coupled to distal tool 911 between first and second control members 1119, 1120 in a similar manner as discussed above in FIGS. 7A-7C.

An appropriate handle assembly (not shown) may be operably coupled to first control member 1119 and second control member 1120 and may manipulate first and second control members 1119, 1120. The handle assembly may be, for example, associated with endoscope 1. As shown in FIG. 9B, the handle assembly may be actuated to retract first control member 1119 in a proximal direction. That is, first control member 1119 may be pulled back, causing pivoting member 1118 to rotate, and thus the deflection of distal tool 911 in a first direction. As shown in FIG. 9C, the handle assembly may be actuated to retract second control member 1120 in a proximal direction (i.e., pulled back), causing pivoting member 1118 to rotate, and thus the deflection of distal tool 911 in a second direction opposite the first direction.

Positioning mechanism 1112 may provide an increased range of motion for distal tool 911. That is, distal tool 911 may be deflected in the first and second directions without being bound by first control member 1119 or second control member 1120 abutting against clevis member 917 or the internal wall of flexible tube 913. In addition, no component of pivoting member 1118 will extend radially outwards, like tangs 928, 1028, and 1080 of the prior embodiments. Accordingly, such increased maneuverability of distal tool 911 allows a greater area of tissue on both sides of distal tool 911 to be treated. Moreover, the increased range of motion may allow distal tool 911 to be proximally deflected and collapsed in a "switch blade" type configuration. Such a collapsed configuration may avoid scraping or damaging the at least one working channel 6 as suction device 1100 is delivered therethrough. It should be appreciated, however, that suction device 1100 may include any suitable restriction means to regulate the range of motion of distal tool 911. For example, the handle assembly may include appropriate stops configured to limit the length of first control member 1119 and/or second control member 1120 that may be retracted. In addition, suction device 1100 may include any suitable stops or limiters to restrict the rotation of pivoting member 1118, and such stops or limiters may be symmetrical or asymmetrical. In other words, such stops or limiters may allow pivoting member 1118 to rotate the same distance in both directions or different distances between both directions.

It should be appreciated that pivot member 918, 1018, and 1118 may be a substantially round shape or any other shape to effectuate deflection of tool 911. In addition pivot 915, 1015, and 1115 may be central or eccentric to pivot member 918, 1018, and 1118. Additionally, in some embodiments, control member 919 may be directly coupled to pivoting member 918, and first and second control members 1019, 1190 may be directly coupled to pivoting member 1018. The attachment between control member 919 and pivoting member 918 and the attachments between first and second control members 1019, 1190 and pivoting member 1018 may allow both pulling and pushing of control member 919 and first and second control members 1019, 1190, or alternatively, only pulling.

FIGS. 10A-10C illustrate another embodiment of a suction device 1500 according to an exemplary disclosed embodiment. Similar to the embodiments of FIGS. 7A-9C, suction device 1500 may include distal tool 911 fluidly coupled to suction tube 914. Suction device 1500 may also include a deflectable elongate member 1501. Elongate member 1501 may be, for example, a catheter, and may be flexible, or may include one or more portions that are flexible, to allow elongate member 1501 to be maneuvered and deflected within the body and traverse tortuous anatomical lumens. For instance, elongate member 1501 may be uniformly flexible or may include a plurality of portions having varying degrees of flexibility or rigidity. Suction device 1500 may also include a hub 1502 configured to couple distal tool 911 and suction tube 914 at a distal tip 1503 of elongate member 1501.

As alluded to above, elongate member 1501 may be comprised of any suitable materials to effectuate active deflection of elongate member 1501. More particularly, at least a distal portion 1504 of elongate member 1501 may be configured to deflect between a substantially linear configuration and a curved, angled, or bent configuration. Distal portion 1504 may be moved to a variety of different curved, angled, or bent configurations in a variety of different directions relative to a longitudinal axis 1516 of elongate member 1501. For example, distal portion 1504 may be configured to deflect in a first direction and a second direction of a first plane (i.e., up and down relative to longitudinal axis 1516), and may be configured to deflect in a first direction and a second direction of a second plane different than the first plane (i.e., left and right relative to longitudinal axis 1516). Accordingly, elongate member 1501 may be configured for at least four-way steering of distal portion 1504. It should also be appreciated, however, that elongate member 1501 may be configured for less or greater than four-way steering of distal portion 1504, depending on, for example, the volume and/or the shape of the internal body anatomies which may be traversed by elongate member 1501.

To provide the active deflection of elongate member 1501, distal portion 1504 may include, for example, a plurality of deflection segments 1557 encased by an outer sleeve 1552, as shown in FIGS. 10A-10C. FIGS. 10A-10C schematically depicts outer sleeve 1552 with dotted lines for the purposes of illustrating the internal layers and elements of elongate member 1501. Deflection segments 1557 may include, for example, a plurality of articulation joints substantially similar to any of the articulation joints disclosed in U.S. Patent Application Publication No. 2010/0076266 to Boulais et al., which is incorporated herein by reference in its entirety. In certain embodiments, deflection segments 1557 may be configured to deflect distal portion 1504 up to 270° relative to longitudinal axis 1516 of elongate member 1501 along the first plane and along the second plane. In other embodiments, deflection segments 1557 may be configured to deflect distal portion 1504 up to 270° relative to longitudinal axis 1516 of elongate member 1501 in one of the first plane and the second plane, and up to 90° relative to longitudinal axis 1516 of elongate member 1501 in the other of the first plane and the second plane. It should be appreciated, however, that distal portion 1504 may be configured to deflect in any suitable angle relative to longitudinal axis 1516.

One or more portions 1505 proximal to distal portion 1504 may be comprised of any suitable materials to provide greater rigidity to elongate member 1501 than distal portion 1504. One or more portions 1505 may include materials configured to provide pushability, stiffness, torquability, and kink resistance to elongate member 1501. For example, one more portions 1505 may include a reinforcement sheath 1506, encased by outer sleeve 1552. The reinforcement sheath 1506 may be reinforced, such as by including a coiled configuration of tightly wound flat wire or polymeric elements. The coiled configuration may provide column strength and torsional rigidity to elongate member 1501 at one or more portions 1505, which may allow elongate member 1501 to be advanced through body lumens and/or cavities. The coiled configuration may also provide kink resistance to prevent one or more portions 1505 from collapsing due to bending forces on one or more portions 1505. In other embodiments, the reinforcement sheath 1506 may include a braided configuration of tightly wound wires or polymeric elements and/or a rigid polymeric sheath formed, for example, high durometer Pebax.

Additionally, or alternatively, one or more portions 1505 may include materials configured to provide passive deflection of elongate member 1501. For example, one or more portions 1505 may include a deflection sheath instead of, or in addition to, reinforcement sheath 1506, encased by outer sleeve 1552, and comprised of a similar coiled configuration of material as reinforcement sheath 1506. The coiled material of deflection sheath, however, may include a suitable cut pattern, such as a laser cut pattern. In other embodiments, the deflection sheath may include a less rigid polymeric sheath formed of, for example, low durometer Pebax.

As discussed, elongate member 1501 may include an outer sleeve 1552 encasing distal portion 1504 and one or more portions 1505. Outer sleeve 1552 may comprise any number of polymer jackets including, as examples, polyethylene, such as polyethylene having a molecular weight in the range of 50,000 to 100,000; nylon, such as nylon 12, nylon 4-6, and nylon 6-6; Pebax (polyether block amides); polyurethane; polytetrafluoroethylene (PTFE); particularly fluorinated ethylene propylene (FEP) copolymers; and polyethylene impregnated with PTFE. Outer sleeve 1552 may vary the stiffness of elongate member 1501, if desired, or may provide improved torque transfer and/or other desirable structural properties. Additionally, outer sleeve 1552 may be used as one convenient method for securing distal portion 1504 and one or more portions 1505 together.

Suction device 1500 may also include one or more control members 1507 extending longitudinally through one or more portions 1505 and distal portion 1504 of elongate member 1501. In an exemplary embodiment, suction device 1500 may include four control members 1507 disposed 90° relative to each other radially around the lumen of elongate member 1501 to provide four-way deflection of distal portion 1504. In other embodiments, suction device 1500 may include two control members 1507 disposed 180° relative to each other radially around the lumen of elongate member 1501 to provide two-way deflection of distal portion 1504. In other embodiments, suction device 1500 may include three control members 1507 disposed 120° relative to each other radially around the lumen of elongate member 1501 to provide three-way deflection of distal portion 1504. It should be appreciated, however, that suction device 1500 may include any number of control members 1507 to control any number of deflection directions of distal portion 1504. Control members 1507 may be constructed of any suitable material, such as stainless steel, tungsten, and Nitinol. Moreover, control members 1507 may be a braided or bundled configuration of a plurality of materials, including, for example, a polymeric tube filled with graphite, or may be a single strand of material, such as a stainless steel wire or conduit.

Control members 1507 may be attached to an inner surface of distal portion 1504, e.g., the inner surfaces of deflection segments 1557, by any suitable fastener, weld, adhesive, or the like at or near the tip of elongate member 1501. Alternatively, control members 1507 may be fastened within the walls of deflection segments 1557, or may be fastened to hub 1502. The proximal ends of control members 1507 may be coupled to an appropriate handle assembly. Accordingly, such a configuration of control members 1507 may facilitate the deflection of distal portion 1504 upon actuation of control members 1507 (i.e., proximal retraction of one or more control members 1507 by the handle assembly). For example, as shown in FIG. 10A, distal portion 1504 may be positioned in a substantially linear configuration when control members 1507 are relaxed or not actuated. As shown in FIG. 10B, upon actuation (i.e., proximal retraction indicated by the arrow) of one of control members 1507, distal portion 1504 may be deflected to a first deflected position. Furthermore, and as shown in FIG. 10C, upon actuation (i.e., proximal retraction indicated by the arrow) of another of control members 1507, distal portion 1504 may be deflected to a second deflected position different than the first deflected position.

FIGS. 11A-11C illustrate another embodiment of a suction device 1600 according to an exemplary disclosed embodiment. Similar to the embodiments of FIGS. 7A-10C, suction device 1600 may include distal tool 911 fluidly coupled to suction tube 914. Suction device 1600 may also include a deflectable elongate member 1601. Similar to elongate member 1501 of FIGS. 10A-10C, elongate member 1601 may be, for example, a catheter, and may be flexible, or may include one or more portions that are flexible, to allow elongate member 1601 to be maneuvered and deflected within the body and traverse tortuous anatomical lumens. For instance, elongate member 1601 may be uniformly flexible or may include a plurality of portions having varying degrees of flexibility or rigidity. Suction device 1600 may also include hub 1502 configured to couple distal tool 911 and suction tube 914 at a distal tip 1603 of elongate member 1601.

Elongate member 1601 may also be comprised of any suitable materials to effectuate active deflection of elongate member 1601. At least a distal portion 1604 of elongate member 1601 may be configured to deflect between a substantially linear configuration and a curved, angled, or bent configuration. Like distal portion 1504 of elongate member 1501, distal portion 1604 of elongate member 1601 may be moved to a variety of different curved, angled, or bent configurations in a variety of different directions relative to a longitudinal axis 91616 of elongate member 1601.

Distal portion 1604 may be composed of any suitable materials configured to provide active deflection. For example, distal portion 1604 may include a deflection sheath 1606 encased by outer sleeve 1552, as shown in FIGS. 11A-11C. FIGS. 11A-11C schematically depicts outer sleeve 1552 with dotted lines for the purposes of illustrating the internal layers and elements of elongate member 1601. Deflection sheath 1606 may include, for example, a polymeric tube having a suitable cut pattern, such as a laser cut pattern, a coiled configuration of material having a laser cut pattern, and/or a polymeric tube formed of a material having low rigidity and high flexibility, such as low durometer Pebax. In certain embodiments, deflection sheath 1606 may be configured to deflect distal portion 1604 up to 270° relative to longitudinal axis 91616 of elongate member 1601 along the first plane and along the second plane. In other embodiments, deflection sheath 1606 may be configured to deflect distal portion 1604 up to 270° relative to longitudinal axis 91616 of elongate member 1601 in one of the first plane and the second plane, and up to 90° relative to longitudinal axis 91616 of elongate member 1601 in the other of the first plane and the second plane. It should be appreciated, however, that distal portion 1604 may be configured to deflect in any suitable angle relative to longitudinal axis 91616.

One or more portions 1605 proximal to distal portion 1604 may be comprised of any suitable materials to provide greater rigidity to elongate member 1601 than distal portion 1604. One or more portions 1605 may include materials configured to provide pushability, stiffness, torquability, and kink resistance to elongate member 1601. For example, one more portions 1605 may include a reinforcement sheath 1626, encased by outer sleeve 1552. The reinforcement sheath 1626 may include a coiled configuration of tightly wound flat wire or polymeric elements. The coiled configuration may provide column strength and torsional rigidity to elongate member 1601 at one or more portions 1605, which may allow elongate member 1601 to be advanced through body lumens and/or cavities. The coiled configuration may also provide kink resistance to prevent one or more portions 1605 from collapsing due to bending forces on one or more portions 1605. In other embodiments, the reinforcement sheath 1626 may include a braided configuration of tightly wound wires or polymeric elements and/or a rigid polymeric sheath formed, for example, high durometer Pebax. Additionally, or alternatively, one or more portions 1605 may include materials configured to provide passive deflection of elongate member 1601.

Like suction device 1500, suction device 1600 may also include one or more control members 1607 extending longitudinally through one or more portions 1605 and distal portion 1604 of elongate member 1601 and configured to facilitate the deflection of distal portion 1604. The distal ends of control members 1607 may be connected to an inner surface of deflection sheath 1606 at or near the tip of elongate member 1601. Alternatively, control members 1607 may be fastened to hub 1502. The proximal ends of control members 1607 may be coupled to an appropriate handle assembly. As shown in FIG. 11A, distal portion 1604 may be positioned in a substantially linear configuration when control members 1607 are relaxed or not actuated. As shown in FIG. 11B, upon actuation (i.e., proximal retraction, as indicated by the arrow) of one of control members 1607 by the handle assembly, distal portion 1604 may be deflected to a first deflected position. Furthermore, and as shown in FIG. 11C, upon actuation (i.e., proximal retraction, as indicated by the arrow) of another of control members 1607, distal portion 1604 may be deflected to a second deflected position different than the first deflected position.

Figure 12:
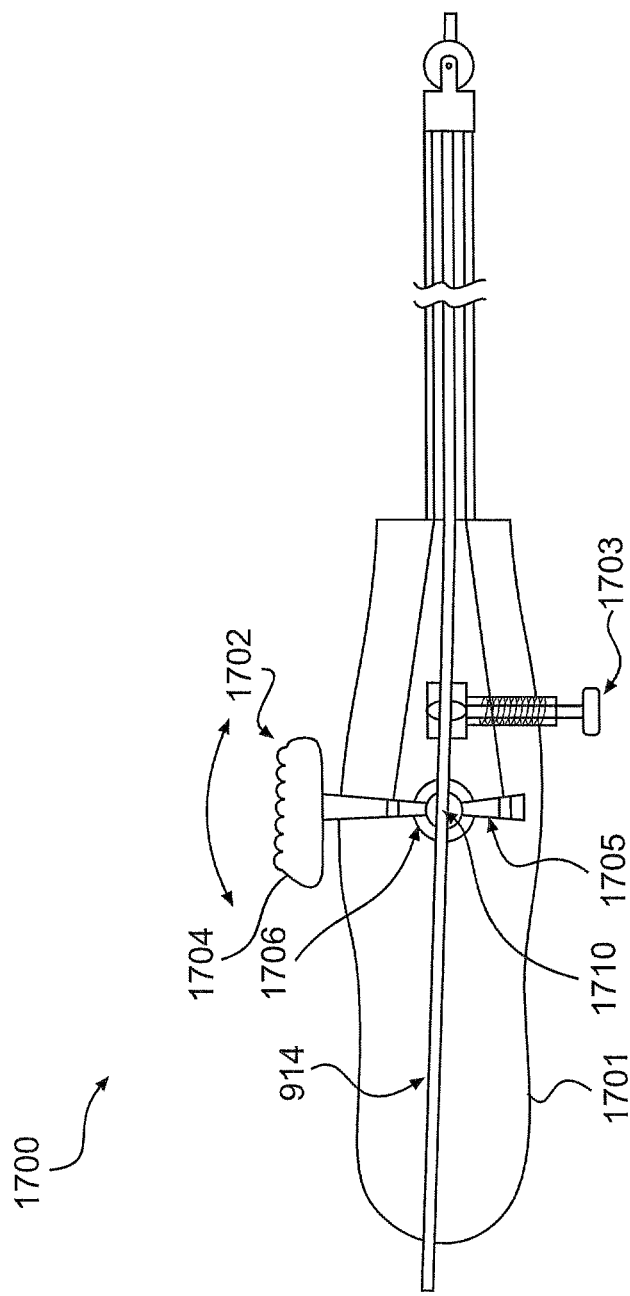
FIG. 12 illustrates a handle assembly for a suction device, according to an exemplary disclosed embodiment.

FIG. 12 illustrates a handle assembly 1700 for suction device 900, 1000, 1100, 1500, 1600. Handle assembly 1700 may include a handle housing 1701 to which flexible tube 913 or elongate member 1501, 1601, a deflection mechanism 1702, and a suction actuator 1703 may be operably coupled.

Deflection mechanism 1702 may include a deflection actuator 1704 configured to control deflection of distal portion 1504, 1604 of elongate member 1501, 1601 (FIGS. 10A-11C) and actuation of positioning mechanism 912, 1012, 1112 (FIGS. 17A-9C). One or more cams 1705 may be coupled to deflection actuator 1704 within handle housing 1701 and may be supported by a frame 1706. One or more cams 1705 may be rotatably supported by a central arm, such as a boss (not shown), and one or more cams 1705 may be rotatable in response to actuation of actuator 1704. More particularly, one or more cams 1705 may pivot about a pivot 1710 upon actuation of actuator 1704.

One or more cams 1705 may be operably coupled to control member 919 (FIGS. 17A-7C); first and second control members 1019, 1190 (FIGS. 8A-8C); first and second control members 1119, 1120 (FIGS. 9A-9C); control members 1507 (FIGS. 10A-10C); or control members 1607 (FIGS. 11A-11C). As such, actuating deflection actuator 1704 may be, for example, a thumb lever configured to move forward or backward (as indicated by the double-headed arrow) to rotate one or more cams 1705, thus selectively effectuating proximal retraction and/or distal advancement of one or more of control member 919 (FIGS. 17A-7C); first and second control members 1019, 1190 (FIGS. 8A-8C); first and second control members 1119, 1120 (FIGS. 9A-9C); control members 1507 (FIGS. 10A-10C); and control members 1607 (FIGS. 11A-11C). Such proximal retraction and/or distal advancement may then deflect distal tool 911. FIG. 12 illustrates that handle assembly 1700 may be appropriate for two-way steering (i.e., deflection in a first plane). It should be appreciated, however, that handle assembly 1700 may also be configured for four-way steering (i.e., deflection in a first plane and a second plane). In such a configuration, handle assembly 1700 may include an additional deflection actuator and an additional rotatable cam, similar to deflection actuator 1704 and one or more cams 1705. The additional rotatable cam may be coupled to one or more control members configured to deflect, for example, distal portion 1504, 1604 of elongate member 1501, 1601. Accordingly, the additional deflection actuator may be actuated by, for example, moving the actuator forward or backward, which may rotate the additional rotatable cam and selectively effectuate proximal retraction of the one or more control members, and thus deflection of distal portion 1504, 1604 in the second plane.

As shown in FIG. 12, suction tube 914 may extend within handle housing 1701 and may connect to a vacuum source (not shown) external handle housing 1701. Although illustrated as terminating at a proximal end of handle assembly 1700, it should be appreciated that suction tube 914 may terminate and connect to the vacuum source at any desired location on handle assembly 1700. Suction actuator 1703 may be operably coupled to suction tube 914 within handle housing 1701 and may be configured to operably open and seal suction through suction tube 914 provided by the vacuum source. For example, suction actuator 1703 may include a spring-biased valve and an actuator, wherein actuation of the actuator may open and close the suction flow through suction tube 914. In certain embodiments, the valve of suction actuator 1703 may be biased to close (or pinch) suction tube 914 and block suction through tube 14. Depressing the actuator of suction actuator 1703 may open the valve and permit suction through tube 14. In other embodiments, suction actuator 1703 may be partially depressed or actuated to partially open the vale and control the amount of suction. In addition, the valve may include any suitable structures, such as knobs, wheels, or levers, that may allow the valve to be in any position between fully-closed and fully-open.

It should also be appreciated that handle assembly 1700 may include an appropriate locking mechanism to lock distal tool 911 in any suitable position. For example, the locking mechanism may secure distal tool 911 in a deflected position, and may release the distal tool 911 from the deflected position when desired. For example, a tightening apparatus may be associated with deflection mechanism 1702 and may be configured to lock the position of actuator 1704.

FIGS. 8A-8E illustrate cup devices for distal tool 911. The cup devices may be outer, hollow containers for housing distal tool 911. The cup devices may be coupled to suction device 900, 1000, 1100, 1500, 1600 and around distal tool 911. A fluid-tight seal may be formed between the cup devices and the portion of suction device 900, 1000, 1100, 1500, 1600 to which the cup devices are coupled (e.g., pivoting member 918, 1018, 1118 and hub 1502). The cup devices may be configured to accommodate the size, shape, and location of the tissue to be suctioned by distal tool 911.

For example, as shown in FIG. 13A, a cup device 1800 may include an opening 1802 at a distal face 1803 of cup device 1800. The opening 1802 may include any desired shape to conform to the type and shape of tissue to be suctioned and grasped. For example, opening 1802 may include a substantially circular shape to more securely and easily grasp substantially circular tissue forms upon aspiration through distal tool 911. Suction through distal tool 911 may also draw the desired tissue sections into opening 1802, securing the tissue section at least partially within cup device 1800. In addition, because opening 1802 is located at distal face 1803 of cup device 1800, tissue sections directly in front of suction device 900, 1000, 1100, 1500, 1600 may be aspirated and grasped.

As shown in FIG. 13B, a cup device 1810 may include an opening 1811 at a side surface 1812 of cup device 1810. Opening 1811 may include a substantially oval shape to more securely and easily grasp substantially oval-shaped tissue forms upon aspiration through distal tool 911. Furthermore, because opening 1811 is located at side surface 1812 of cup device 1810, tissue sections on the sides of suction device 900, 1000, 1100, 1500, 1600 may be aspirated and grasped. Moreover, because opening 1811 may be normal to the direction of aspiration (i.e., intersecting distal tool 911), the aspiration and grasping force may be stronger.

As shown in FIG. 13C, a cup device 1820 may include an opening 1821 at a side surface 1822 of cup device 1820. Cup device 1820 may also include a substantially cylindrical shape. Opening 1821 may include a substantially elongated shape substantially parallel to the longitudinal axis of distal tube 11. Opening 1821 may therefore more securely and easily grasp substantially elongated areas of tissue extending substantially parallel to distal tool 911 upon aspiration through distal tool 911. Furthermore, because opening 1821 is located at side surface 1822 of cup device 1820, tissue sections on the sides of suction device 900, 1000, 1100, 1500, 1600 may be aspirated and grasped, and the aspiration and grasping force may be greater.

As shown in FIG. 13D, a cup device 1830 may include an opening 1831 at a side surface 1832 of cup device 1830. Cup device 1830 may also include a substantially frustoconical shape. Opening 1831 may include a substantially elongated shape and may be substantially normal to the longitudinal axis of distal tool 911. Opening 1831 may therefore more securely and easily grasp substantially elongated areas of tissue extending substantially perpendicular to distal tool 911 upon aspiration through distal tool 911. Furthermore, because opening 1831 is located at side surface 1832 of cup device 1830, tissue sections on the sides of suction device 900, 1000, 1100, 1500, 1600 may be aspirated and grasped, and the aspiration and grasping force may be greater.

As shown in FIG. 13E, a cup device 1840 may include an opening 1841 positioned at an angle to a longitudinal axis of cup device 1840. Opening 1841 may include a substantially circular shape to more securely and easily grasp substantially circular tissue forms upon aspiration through distal tool 911. Furthermore, because opening 1841 is at an angled configuration, tissue sections directly in front of and on the sides of suction device 900, 1000, 1100, 1500, 1600 may be aspirated and grasped.

It should be appreciated that cup devices 1800, 1810, 1820, 1830, and 1840 may be hollow, yet formed of any suitable material that may be sufficiently rigid to prevent the collapse of cup devices 1800, 1810, 1820, 1830, and 1840 from the suction force applied by distal tool 911. Moreover, cup devices 1800, 1810, 1820, 1830, and 1840 may be formed of any suitable transparent material to allow visualization of the grasped area.

As will be appreciated by one of ordinary skill in the art, the presently disclosed suction devices 900, 1000, 1100, 1500, 1600 may enjoy numerous advantages. First, for example, distal tool 911 may be adjusted independently of endoscope 1, that is, the position of distal tool 911 may be altered by manipulating positioning mechanism 912, 1012, 1112 or control members 1507, 607, without the need to articulate, steer, shift, pull, and/or push endoscope 1. Therefore, finer control of the position of distal tool 911 may be provided to a physician. In addition, the physician may be able to maneuver and control suction device 900, 1000, 1100, 1500, 1600, without assistance from a second operator, such as another physician or a physician's assistant. The physician may directly and simultaneously control the position and activation (i.e., aspiration) of suction device 900, 1000, 1100, 1500, 1600. Moreover, when using suction device 900, 1000, 1100, 1500, 1600 with an endoscope housing multiple tools, the position of suction device 900, 1000, 1100, 1500, 1600 may be independently controlled without moving the other tools, since the entire endoscope need not be manipulated to position suction device 900, 1000, 1100, 1500, 1600.

In certain other embodiments, the distal tool may serve as a guide for other endoscopic tools inserted into body anatomies. For example, an electrocautery loop may be fed through an insertion tube coupled to the distal tool. The electrocautery loop may then exit the distal tool to reach target tissue. By actuating the positioning mechanism, the distal tool, and thus the electrocautery loop, may be deflected to a desired position.

Moreover, it should be appreciated that any of devices 900, 1000, 1100, 1500, and 1600 may include an imaging system for visualizing the body anatomies. The imaging system may include any suitable system for capturing images within body anatomies, such as, for example, an optical fiber and/or an electronic camera including illumination units. Accordingly, devices 900, 1000, 1100, 1500, and 1600 may then be used without endoscope 1 for visualization purposes. Nevertheless, employing devices 900, 1000, 1100, 1500, and 1600 having an imaging system with endoscope 1 may provide multiple areas of visualization, including one area from endoscope 1 and another area from devices 900, 1000, 1100, 1500, and 1600.

In certain embodiments, device 900, 1000, 1100, 1500, 1600 may be delivered through working channel 6 of endoscope 1 to an area at or near target tissue to be grasped. Distal tool 911 may then be deflected towards the target tissue and suction may be applied through distal tool 911. It should be appreciated that a foot pedal or a button associated with the vacuum source may be actuated to activate suction. Suction through distal tool 911 may induce negative pressures to grasp the target tissue. Positive pressure or lack of negative pressure effectuated by, for example, depression of suction actuator 1703 or appropriate actuation of the foot pedal or the button of the vacuum source, may release the target tissue. Once the target tissue is grasped, distal tool 911 may be deflected to a desired position to manipulate the target tissue. For example, distal tool 911 may be deflected to retract the target tissue by pulling and/or pushing the target tissue. Distal tool 911 may also be deflected to position the target tissue such that another tool, such as a knife, a dissector, or scissors, delivered through another working channel 6 of endoscope 1 may more easily reach the target tissue and cut, dissect, and/or resect the target tissue.

It should be appreciated that in any of the embodiments described herein, distal tool 911 may be, in an initial or default position, offset from the longitudinal axis of the suction device and deflected to any desired position. Furthermore, distal tool 911 may be formed of a conductive material and may be configured for electrocautery applications. In addition, device 900, 1000, 1100, 1500, 1600 may serve as an infusion device to deliver any suitable liquid or gas through distal tool 911. Moreover, distal tool 911 may any suitable flexibility feature. For example, a proximal portion of distal tool 911 (e.g., a portion connected to pivoting members, 918, 1018, 1118 and hub 1502) may be comprised of a softer or more flexible material than the remaining portion of distal tool 911 or may include bellows. In some embodiments, then entire length of distal tool 911 except for the proximal portion may be reinforced with any suitable material or method. In addition, a lumen may extend though pivoting members 918, 1018, 1118 and hub 1502 to fluidly couple distal tool 911 to suction tube 914.

Any aspect set forth in any embodiment may be used with any other embodiment set forth herein. Every device and apparatus set forth herein may be used in any suitable medical procedure, may be introduced an utilized though any suitable introducer, endoscope, and/or guide tube, may be advanced through any suitable body lumen and body cavity, and may be used for treatment of any suitable body portion. For example, the apparatuses and methods described herein may be used in any natural body lumen or tract, including those accessed orally, vaginally, or rectally, or may be used via percutaneous applications.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A medical device, comprising:
   a handle assembly;
   a shaft extending from the handle assembly, wherein the shaft includes:
   a flexible distal portion having a distal end,
   an outer sheath having a first passage extending therethrough,
   an inner sheath having a second passage extending therethrough, wherein the outer sheath circumferentially surrounds the inner sheath,
   a wire that extends through the first passage of the outer sheath, and
   a hub at the distal end of the distal portion, wherein the wire is coupled to the hub, wherein the inner sheath is coupled to the hub, wherein the hub defines a first lumen, and wherein the first lumen of the hub is in fluid communication with the second passage of the inner sheath; and
   a tool coupled to the hub, wherein the tool extends distally from the hub, and wherein the tool includes:
   a tube having a second lumen passing therethrough, wherein the second lumen of the tube is in fluid communication with the first lumen of the hub, and wherein, along at least a segment of the tube, a cross-sectional width of the tube does not increase between a proximal end of the segment and a distal end of the segment, and
   a distalmost face that is wider than the segment of the tube, and wherein the distalmost face defines a distally-facing aperture.

2. The medical device of claim 1, wherein the distally-facing aperture opens into the second lumen of the tube.

3. The medical device of claim 1, wherein a width of the distalmost face and the cross-sectional width of the segment of the tube are measured in a direction perpendicular to a central longitudinal axis of the tool.

4. The medical device of claim 1, wherein the distally-facing aperture is circular.

5. The medical device of claim 1, wherein the distalmost face is planar.

6. The medical device of claim 5, wherein the distalmost face is perpendicular to a central longitudinal axis of the tool.

7. The medical device of claim 1, wherein the tool includes an electrically conductive material.

8. The medical device of claim 7, wherein the wire is formed of a conductive material and is configured to provide electricity to the tool.

9. The medical device of claim 8, wherein the wire is directly coupled to the hub, and wherein the wire is offset from a central longitudinal axis of the shaft.

10. The medical device of claim 1, wherein the inner sheath and the tube are configured to deliver fluid from the second passage of the inner sheath to the second lumen of the tube.

11. A medical device, comprising:
    a handle assembly;
    a shaft extending from the handle assembly, wherein the shaft includes:
    a flexible distal portion having a distal end,
    an outer sheath having a first passage extending therethrough,
    an inner sheath having a second passage extending therethrough,
    a hub at the distal end of the distal portion, wherein the hub is coupled to the inner sheath, and wherein the hub defines a first lumen; and
    a tool coupled to the hub, wherein the tool extends distally from the hub, and wherein the tool includes:
    a cylindrical proximal section having a second lumen passing therethrough, wherein, along at least a segment of the cylindrical proximal section, a cross-sectional width of the cylindrical proximal section does not increase between a proximal end of the segment and a distal end of the segment, and
    a distalmost face that is wider than the segment, wherein the distalmost face defines a distally-facing aperture;
    wherein the first lumen of the hub is configured to fluidly couple the second passage of the inner sheath to the second lumen of the cylindrical proximal section.

12. The medical device of claim 11, wherein the distally-facing aperture is in communication with the second lumen of the cylindrical proximal section.

13. The medical device of claim 11, wherein the cylindrical proximal section includes an electrically conductive material, and wherein the shaft further includes a conductive wire coupled to the hub and configured to transmit electricity to the cylindrical proximal section.

14. A medical device, comprising:
    a handle assembly;
    a shaft extending from the handle assembly, wherein the shaft includes:
    a bendable distal portion, wherein the distal portion has a distal end,
    an outer sheath having a first passage extending therethrough,
    an inner sheath having a second passage extending therethrough,
    a hub at the distal end of the distal portion, wherein the inner sheath is coupled to the hub; and
    a tool coupled to the hub, wherein the tool extends distally from the hub, and wherein the tool includes:
    a tube having a first lumen passing therethrough, wherein the tube includes a segment having:
    a proximal end, and
    a distal end, wherein a cross-sectional width of the distal end of the segment is not wider than a cross-sectional width of the proximal end, and
    a distalmost face wider than the distal end of the segment, wherein the distalmost face defines a distally-facing aperture;
    wherein the second passage of the inner sheath and the first lumen of the tube are in fluid communication via a second lumen of the hub.

15. The medical device of claim 14, wherein the cross-sectional width of the proximal end is equal to the cross-sectional width of the distal end of the segment.

16. The medical device of claim 14, wherein the first lumen of the tube is in fluid communication with the distally-facing aperture.

17. The medical device of claim 14, wherein the tool includes a proximally-facing, planar surface that is perpendicular to a central longitudinal axis of the tool.

18. The medical device of claim 17, wherein the tool further includes a neck portion that is narrower than the proximally-facing, planar surface, wherein the neck portion is proximal of and terminates at the proximally-facing, planar surface.

19. The medical device of claim 14, wherein the tube is formed of conductive material, and wherein the shaft also includes a conductive wire coupled to the hub and configured to transmit electricity to the tube.

20. The medical device of claim 14, wherein the inner sheath and the tube are configured to deliver fluid from the second passage of the inner sheath to the first lumen of the tube.

* * * * *